United States Patent
Fu et al.

(10) Patent No.: US 7,572,437 B2
(45) Date of Patent: Aug. 11, 2009

(54) LONG ACTING HUMAN INTERFERON ANALOGS

(76) Inventors: Yan Fu, FortuneRock, In., 3120 Saint Paul St., Suite 109D, Baltimore, MD (US) 21218; Zailin Yu, FortuneRock, Inc., 3120 Saint Paul St., Suite 109D, Baltimore, MD (US) 21218

( * ) Notice: Subject to any disclaimer, the term of this patent is extended or adjusted under 35 U.S.C. 154(b) by 1403 days.

(21) Appl. No.: 10/851,666

(22) Filed: May 24, 2004

(65) Prior Publication Data

US 2009/0053173 A1    Feb. 26, 2009

Related U.S. Application Data

(63) Continuation-in-part of application No. 10/609,346, filed on Jun. 26, 2003, now Pat. No. 7,244,833.

(60) Provisional application No. 60/483,984, filed on Jun. 30, 2003, provisional application No. 60/392,948, filed on Jul. 1, 2002.

(51) Int. Cl.
  *A61K 38/21*  (2006.01)
  *A61K 39/00*  (2006.01)
  *A61K 45/00*  (2006.01)
  *C07H 21/02*  (2006.01)

(52) U.S. Cl. .................. 424/85.4; 424/192.1; 424/85.1; 536/23.52

(58) Field of Classification Search ................. 424/85.4, 424/192.1, 85.1; 536/23.52
See application file for complete search history.

*Primary Examiner*—Fereydoun G Sajjadi
(74) *Attorney, Agent, or Firm*—Yi Li

(57) ABSTRACT

Compositions, kits and methods are provided for Interferon analogs in order to promote general health or for therapeutic treatment of diseases. Human interferon analogs are made by fusion of interferon with human serum albumin. The bioassay shows that the interferon analogs with the same cell protection against viral attack have 3-10 times longer acting function than interferon in vivo. These novel long acting interferon analogs can be used in treatment of patients with viral infection, such as SARS virus, HIV, HCV, HBV, or HAV, and the cancer diseases, such as leukemia and malignant melanoma. They also have a 3-5 times longer shelf-life compared with interferon.

14 Claims, 14 Drawing Sheets

Figure 1

(A) Seq ID No. 1 DNA Sequence Encoding of Human Interferon Analog, HSA-IFN-α-1b

```
ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTATGTGATCTCCCTGAGACCC
ACAGCCTGGATAACAGGAGGACCTTGATGCTCCTGGCACAAATGAGCAGAATCTCTCCTTCCTCCTGTCTG
ATGGACAGACATGACTTTGGATTTCCCCAGGAGGAGTTTGATGGCAACCAGTTCCAGAAGGCTCCAGCCAT
CTCTGTCCTCCATGAGCTGATCCAGCAGATCTTCAACCTCTTTACCACAAAAGATTCATCTGCTGCTTGGG
ATGAGGACCTCCTAGACAAATTCTGCACCGAACTCTACCAGCAGCTGAATGACTTGGAAGCCTGTGTGATG
CAGGAGGAGAGGGTGGGAGAAACTCCCCTGATGAATGCGGACTCCATCTTGGCTGTGAAGAAATACTTCCG
AAGAATCACTCTCTATCTGACAGAGAAGAAATACAGCCCTTGTGCCTGGGAGGTTGTCAGAGCAGAAATCA
TGAGATCCCTCTCTTTATCAACAAACTTGCAAGAAAGATTAAGGAGGAAGTAA
```

(B). Seq ID No.2. Amino Acid Sequence of Human Interferon Analog, HSA-IFN-α-1b

```
DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLCDLPETHSLDNRRTLMLLAQMSRISPSSCLMDRHDFGFPQEEFDGNQFQKAPAI
SVLHELIQQIFNLFTTKDSSAAWDEDLLDKFCTELYQQLNDLEACVMQEERVGETPLMNADSILAVKKYFR
RITLYLTEKKYSPCAWEVVRAEIMRSLSLSTNLQERLRRK.
```

Figure 1-continued (C). Seq ID No.3 DNA Sequence Encoding of Human Interferon Analog, HSA-IFN-α-2b

```
ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTATGTGATCTGCCTCAAACCC
ACAGCCTGGGTAGCAGGAGGACCTTGATGCTCCTGGCACAGATGAGGAaAATCTCTCTTTTCTCCTGCTTG
AAGGACAGACATGACTTTGGATTTCCCCAGGAGGAGTTTGGCAACCAGTTCCAAAAGGCTGAAACCATCCC
TGTCCTCCATGAGATGATCCAGCAGATCTTCAATCTCTTCAGCACAAAGGACTCATCTGCTGCTTGGGATG
AGACCCTCCTAGACAAATTCTACACTGAACTCTACCAGCAGCTGAATGACCTGGAAGCCTGTGTGATACAG
GGGGTGGGGGTGACAGAGACTCCCCTGATGAAGGAGGACTCCATTCTGGCTGTGAGGAAATACTTCCAAAG
AATCACTCTCTATCTGAAAGAGAAGAAATACAGCCCTTGTGCCTGGGAGGTTGTCAGAGCAGAAATCATGA
GATCTTTTTCTTTGTCAACAAACTTGCAAGAAAGTTTAAGAAGTAAGGAATGA
```

(D) Seq ID No. 4. Amino Acid Sequence of Human Interferon Analog, HSA-IFN-α-2b

```
DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLCDLPQTHSLGSRRTLMLLAQMRkISLFSCLKDRHDFGFPQEEFGNQFQKAETIP
VLHEMIQQIFNLFSTKDSSAAWDETLLDKFYTELYQQLNDLEACVIQGVGVTETPLMKEDSILAVRKYFQR
ITLYLKEKKYSPCAWEVVRAEIMRSFSLSTNLQESLRSKE
```

Figure 1-continued (E) Seq ID No. 5. DNA Sequence Encoding of Human Interferon Analog, HSA-IFN-β

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTA<u>tacaacttgcttggattcc
tacaaagaagcagcaattttcagtgtcagaagctcctgtggcaattgaatgggaggcttgaatactgcctc
aaggacaggatgaactttgacatccctgaggagattaagcagctgcagcagttccagaaggaggacgccgc
attgaccatctatgagatgctccagaacatctttgctatttcagacaagattcatctagcactggctgga
atgagactattgttgagaacctcctggctaatgtctatcatcagataaaccatctgaagacagtcctggaa
gaaaaactggagaaagaagatttcaccaggggaaaactcatgagcagtctgcacctgaaaagatattatgg
gaggattctgcattacctgaaggccaaggagtacagtcactgtgcctggaccatagtcagagtggaaatcc
taaggaacttttacttcattaacagacttacaggttacctccgaaactga</u>

(F) Seq ID No. 6. Amino Acid Sequence of Human Interferon Analog, HSA-IFN-β

DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGL<u>YNLLGFLQRSSNFQCQKLLWQLNGRLEYCLKDRMNFDIPEEIKQLQQFQKEDAA
LTIYEMLQNIFAIFRQDSSSTGWNETIVENLLANVYHQINHLKTVLEEKLEKEDFTRGKLMSSLHLKRYYG
RILHYLKAKEYSHCAWTIVRVEILRNFYFINRLTGYLRN</u>

Figure 1-continued

(G) Seq ID No. 7. DNA Sequence Encoding Human Interferon Analog, HSA-IFN-ω

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTAtgtgatctgcctcagaacc
atggcctacttagcaggaacaccttggtgcttctgcaccaaatgaggagaatctcccctttcttgtgtctc
aaggacagaagagacttcaggttcccccaggagatggtaaaagggagccagttgcagaaggcccatgtcat
gtctgtcctccatgagatgctgcagcagatcttcagcctcttccacacagagcgctcctctgctgcctga
acatgaccctcctagaccaactccacactggacttcatcagcaactgcaacacctggagacctgcttgctg
caggtagtgggagaaggagaatctgctgggcaattagcagccctgcactgaccttgaggaggtacttcca
gggaatccgtgtctacctgaaagagaagaaatacagcgactgtgcctgggaagttgtcagaatggaaatca
tgaaatccttgttcttatcaacaaacatgcaagaaagactgagaagtaaagatagagacctgggctcatct
tga (H) Seq ID No. 8. Amino Acid Sequence of Human Interferon Analog, HSA-IFN-ω

DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLCDLPQNHGLLSRNTLVLLHQMRRISPFLCLKDRRDFRFPQEMVKGSQLQKAHVM
SVLHEMLQQIFSLFHTERSSAAWNMTLLDQLHTGLHQQLQHLETCLLQVVGEGESAGAISSPALTLRRYFQ
GIRVYLKEKKYSDCAWEVVRMEIMKSLFLSTNMQERLRSKDRDLGSS

Figure 1-continued

(I) Seq ID No. 9. DNA Sequence Encoding of Human Interferon Analog, HSA-IFN-γ

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTAcaggacccatatgtacaag
aagcagaaaaccttaagaaatattttaatgcaggtcattcagatgtagcggataatggaactcttttctta
ggcattttgaagaattggaaagaggagagtgacagaaaaataatgcagagccaaattgtctccttttactt
caaactttttaaaaactttaaagatgaccagagcatccaaaagagtgtggagaccatcaaggaagacatga
atgtcaagttttcaatagcaacaaaaagaaacgagatgacttcgaaaagctgactaattattcggtaact
gacttgaatgtccaacgcaaagcaatacatgaactcatccaagtgatggctgaactgtcgccagcagctaa
aacagggaagcgaaaaaggagtcagatgctgtttcgaggtcgaagagcatcccagtaa (J) Seq ID No. 10. Amino Acid Sequence of Human Interferon Analog, HSA-IFN-γ

DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLQDPYVQEAENLKKYFNAGHSDVADNGTLFLGILKNWKEESDRKIMQSQIVSFYF
KLFKNFKDDQSIQKSVETIKEDMNVKFFNSNKKKRDDFEKLTNYSVTDLNVQRKAIHELIQVMAELSPAAK
TGKRKRSQMLFRGRRASQ

Figure 1-continued (K) Seq ID No. 11. DNA Sequence Encoding Human Serum Albumin (HSA)

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTATAA (L) Seq ID No. 12. Amino Acid Sequence of Human Serum Albumin (HSA)

MKWVTFISLLFLFSSAYSRGVFRRDAHKSEVAHRFKDLGEENFKALVLIAFAQYLQQCPFEDHVKLVNEVT
EFAKTCVADESAENCDKSLHTLFGDKLCTVATLRETYGEMADCCAKQEPERNECFLQHKDDNPNLPRLVRP
EVDVMCTAFHDNEETFLKKYLYEIARRHPYFYAPELLFFAKRYKAAFTECCQAADKAACLLPKLDELRDEG
KASSAKQRLKCASLQKFGERAFKAWAVARLSQRFPKAEFAEVSKLVTDLTKVHTECCHGDLLECADDRADL
AKYICENQDSISSKLKECCEKPLLEKSHCIAEVENDEMPADLPSLAADFVESKDVCKNYAEAKDVFLGMFL
YEYARRHPDYSVVLLLRLAKTYETTLEKCCAAADPHECYAKVFDEFKPLVEEPQNLIKQNCELFEQLGEYK
FQNALLVRYTKKVPEVSTPTLVEVSRNLGKVGSKCCKHPEAKRMPCAEDYLSVVLNQLCVLHEKTPVSDRV
TKCCTESLVNRRPCFSALEVDETYVPKEFNAETFTFHADICTLSEKERQIKKQTALVELVKHKPKATKEQL
KAVMDDFAAFVEKCCKADDKETCFAEEGKKLVAASQAALGL (M) Seq ID No. 13. DNA Sequence Encoding Human Interferon-α-1b ATGGCCTTGACCTTTGCTTTACTGGTGGCCCTCCTGGTGCTCAGCTGCAAGTCAAGCTGCTCTGTGGGCTG
TGATCTGCCTCAAACCCACAGCCTGGGTAGCAGGAGGACCTTGATGCTCCTGGCACAGATGAGGAGAATCT
CTCTTTTCTCCTGCTTGAAGGACAGACATGACTTTGGATTTCCCCAGGAGGAGTTTGGCAACCAGTTCCAA
AAGGCTGAAACCATCCCTGTCCTCCATGAGATGATCCAGCAGATCTTCAATCTCTTCAGCACAAAGGACTC
ATCTGCTGCTTGGGATGAGACCCTCCTAGACAAATTCTACACTGAACTCTACCAGCAGCTGAATGACCTGG
AAGCCTGTGTGATACAGGGGGTGGGGGTGACAGAGACTCCCCTGATGAAGGAGGACTCCATTCTGGCTGTG
AGGAAATACTTCCAAAGAATCACTCTCTATCTGAAAGAGAAGAAATACAGCCCTTGTGCCTGGGAGGTTGT
CAGAGCAGAAATCATGAGATCTTTTTCTTTGTCAACAAACTTGCAAGAAAGTTTAAGAAGTAAGGAATGA

Figure 1-continued

(N) Seq ID No. 14. Amino Acid Sequence of Human Interferon-α-1b

MALTFALLVALLVLSCKSSCSVGCDLPQTHSLGSRRTLMLLAQMRRISLFSCLKDRHDFGFPQEEFGNQFQ
KAETIPVLHEMIQQIFNLFSTKDSSAAWDETLLDKFYTELYQQLNDLEACVIQGVGVTETPLMKEDSILAV
RKYFQRITLYLKEKKYSPCAWEVVRAEIMRSFSLSTNLQESLRSKE

(O) Seq ID No. 15. DNA Sequence Encoding Human Interferon-α-2b

ATGGCCTTGACCTTTGCTTTACTGGTGGCCCTCCTGGTGCTCAGCTGCAAGTCAAGCTGCTCTGTGGGCTG
TGATCTGCCTCAAACCCACAGCCTGGGTAGCAGGAGGACCTTGATGCTCCTGGCACAGATGAGGAAAATCT
CTCTTTTCTCCTGCTTGAAGGACAGACATGACTTTGGATTTCCCCAGGAGGAGTTTGGCAACCAGTTCCAA
AAGGCTGAAACCATCCCTGTCCTCCATGAGATGATCCAGCAGATCTTCAATCTCTTCAGCACAAAGGACTC
ATCTGCTGCTTGGGATGAGACCCTCCTAGACAAATTCTACACTGAACTCTACCAGCAGCTGAATGACCTGG
AAGCCTGTGTGATACAGGGGGTGGGGGTGACAGAGACTCCCCTGATGAAGGAGGACTCCATTCTGGCTGTG
AGGAAATACTTCCAAAGAATCACTCTCTATCTGAAAGAGAAGAAATACAGCCCTTGTGCCTGGGAGGTTGT
CAGAGCAGAAATCATGAGATCTTTTTCTTTGTCAACAAACTTGCAAGAAAGTTTAAGAAGTAAGGAATGA

(P) Seq ID No. 16. Amino Acid Sequence of Human Interferon-α-2b

MALTFALLVALLVLSCKSSCSVGCDLPQTHSLGSRRTLMLLAQMRkISLFSCLKDRHDFGFPQEEFGNQFQ
KAETIPVLHEMIQQIFNLFSTKDSSAAWDETLLDKFYTELYQQLNDLEACVIQGVGVTETPLMKEDSILAV
RKYFQRITLYLKEKKYSPCAWEVVRAEIMRSFSLSTNLQESLRSKE

(Q) Seq ID No. 17. DNA Sequence Encoding Human Interferon-β

ATGACCAACAAGTGTCTCCTCCAAATTGCTCTCCTGTTGTGCTTCTCCACTACAGCTCTTTCCATGAGCTA
CAACTTGCTTGGATTCCTACAAAGAAGCAGCAATTTTCAGTGTCAGAAGCTCCTGTGGCAATTGAATGGGA
GGCTTGAATACTGCCTCAAGGACAGGATGAACTTTGACATCCCTGAGGAGATTAAGCAGCTGCAGCAGTTC
CAGAAGGAGGACGCCGCATTGACCATCTATGAGATGCTCCAGAACATCTTTGCTATTTTCAGACAAGATTC
ATCTAGCACTGGCTGGAATGAGACTATTGTTGAGAACCTCCTGGCTAATGTCTATCATCAGATAAACCATC
TGAAGACAGTCCTGGAAGAAAAACTGGAGAAAGAAGATTTCACCAGGGGAAAACTCATGAGCAGTCTGCAC
CTGAAAAGATATTATGGGAGGATTCTGCATTACCTGAAGGCCAAGGAGTACAGTCACTGTGCCTGGACCAT
AGTCAGAGTGGAAATCCTAAGGAACTTTTACTTCATTAACAGACTTACAGGTTACCTCCGAAACTGA

(R) Seq ID No. 18. Amino Acid Sequence of Human Interferon-β

MTNKCLLQIALLLCFSTTALSMSYNLLGFLQRSSNFQCQKLLWQLNGRLEYCLKDRMNFDIPEEIKQLQQF
QKEDAALTIYEMLQNIFAIFRQDSSSTGWNETIVENLLANVYHQINHLKTVLEEKLEKEDFTRGKLMSSLH
LKRYYGRILHYLKAKEYSHCAWTIVRVEILRNFYFINRLTGYLRN

(S) Seq ID No. 19. DNA Sequence Encoding Human Interferon-ω

ATGGCCCTCCTGTTCCCTCTACTGGCAGCCCTAGTGATGACCAGCTATAGCCCTGTTGGATCTCTGGGCTG
TGATCTGCCTCAGAACCATGGCCTACTTAGCAGGAACACCTTGGTGCTTCTGCACCAAATGAGGAGAATCT
CCCCTTTCTTGTGTCTCAAGGACAGAAGAGACTTCAGGTTCCCCCAGGAGATGGTAAAAGGGAGCCAGTTG
CAGAAGGCCCATGTCATGTCTGTCCTCCATGAGATGCTGCAGCAGATCTTCAGCCTCTTCCACACAGAGCG
CTCCTCTGCTGCCTGGAACATGACCCTCCTAGACCAACTCCACACTGGACTTCATCAGCAACTGCAACACC
TGGAGACCTGCTTGCTGCAGGTAGTGGGAGAAGGAGAATCTGCTGGGCAATTAGCAGCCCTGCACTGACC
TTGAGGAGGTACTTCCAGGGAATCCGTGTCTACCTGAAAGAGAAGAAATACAGCGACTGTGCCTGGGAAGT

Figure 1-continued

TGTCAGAATGGAAATCATGAAATCCTTGTTCTTATCAACAAACATGCAAGAAAGACTGAGAAGTAAAGATA
GAGACCTGGGCTCATCTTGA (T) Seq ID No. 20. Amino Acid Sequence of Human Interferon-ω

MALLFPLLAALVMTSYSPVGSLGCDLPQNHGLLSRNTLVLLHQMRRISPFLCLKDRRDFRFPQEMVKGSQL
QKAHVMSVLHEMLQQIFSLFHTERSSAAWNMTLLDQLHTGLHQQLQHLETCLLQVVGEGESAGAISSPALT
LRRYFQGIRVYLKEKKYSDCAWEVVRMEIMKSLFLSTNMQERLRSKDRDLGSS (U) Seq ID No. 21. DNA Sequence Encoding Human Interferon-γ

ATGAAATATACAAGTTATATCTTGGCTTTTCAGCTCTGCATCGTTTTGGGTTCTCTTGGCTGTTACTGCCA
GGACCCATATGTACAAGAAGCAGAAAACCTTAAGAAATATTTTAATGCAGGTCATTCAGATGTAGCGGATA
ATGGAACTCTTTTCTTAGGCATTTTGAAGAATTGGAAAGAGGAGAGTGACAGAAAAATAATGCAGAGCCAA
ATTGTCTCCTTTTACTTCAAACTTTTTAAAAACTTTAAAGATGACCAGAGCATCCAAAAGAGTGTGGAGAC
CATCAAGGAAGACATGAATGTCAAGTTTTTCAATAGCAACAAAAAGAAACGAGATGACTTCGAAAAGCTGA
CTAATTATTCGGTAACTGACTTGAATGTCCAACGCAAAGCAATACATGAACTCATCCAAGTGATGGCTGAA
CTGTCGCCAGCAGCTAAAACAGGGAAGCGAAAAAGGAGTCAGATGCTGTTTCGAGGTCGAAGAGCATCCCA
GTAA (V) Seq ID No. 22. Amino Acid Sequence of Human Interferon-γ

MKYTSYILAFQLCIVLGSLGCYCQDPYVQEAENLKKYFNAGHSDVADNGTLFLGILKNWKEESDRKIMQSQ
IVSFYFKLFKNFKDDQSIQKSVETIKEDMNVKFFNSNKKKRDDFEKLTNYSVTDLNVQRKAIHELIQVMAE
LSPAAKTGKRKRSQMLFRGRRASQ

Figure 6.
A.
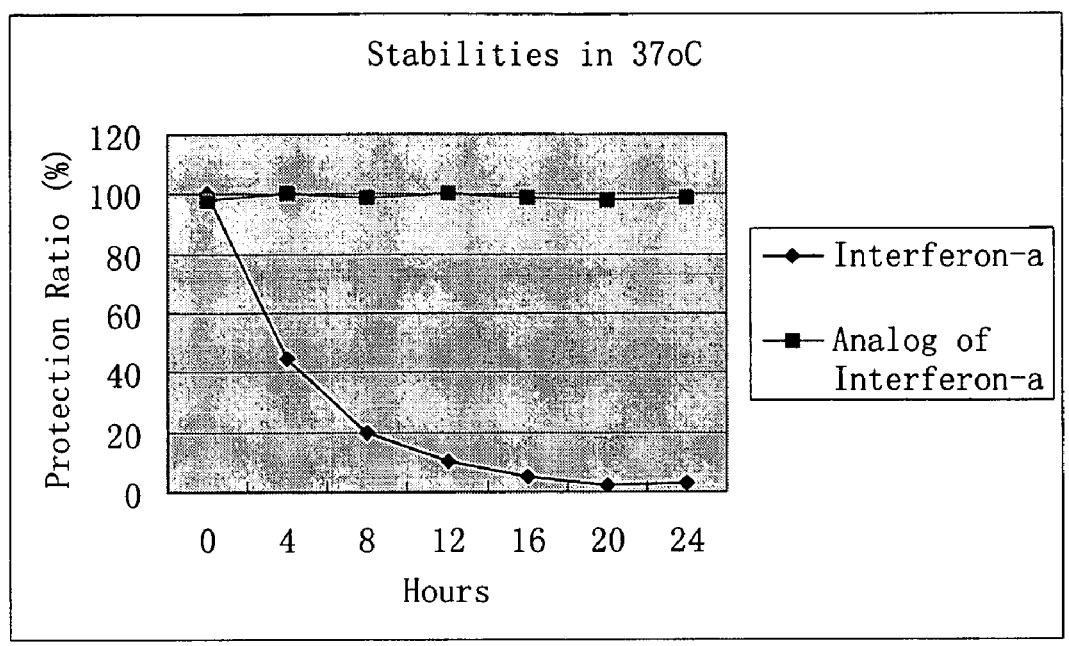
B.
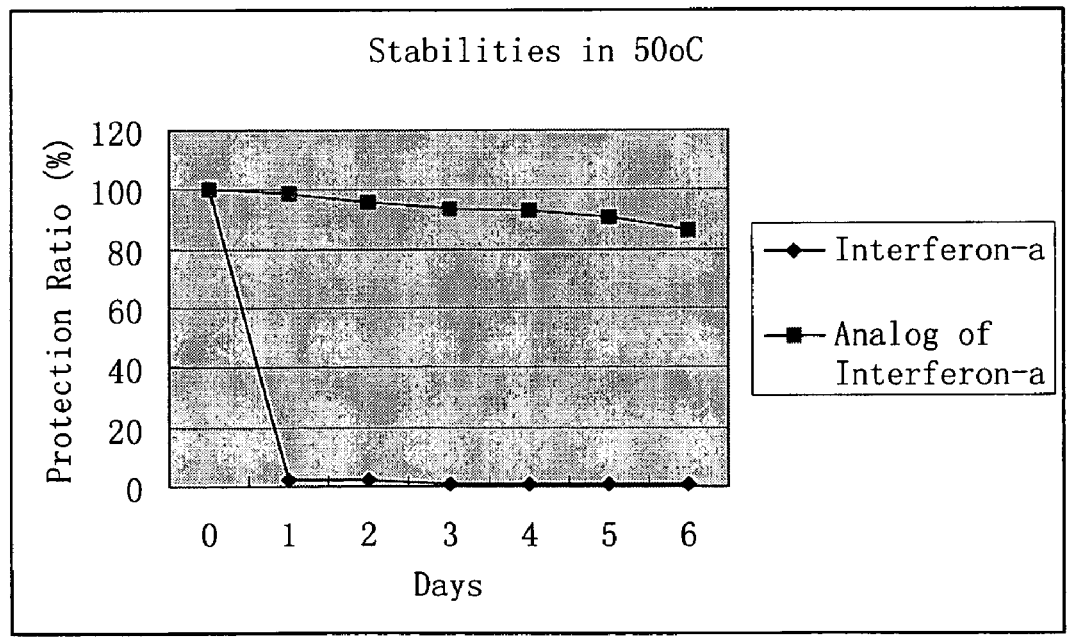

Figure 7.
A. Long Acting of IFN-α-2b Analog (After Injection: Hours)
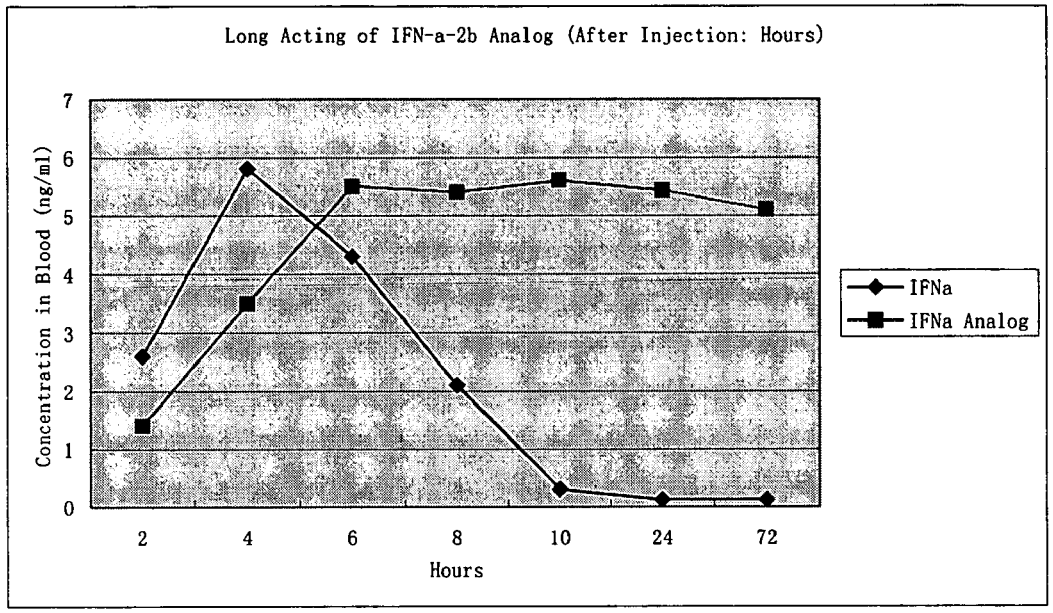
B. Long Acting of IFN-α-2b Analog (After Injection: Days)
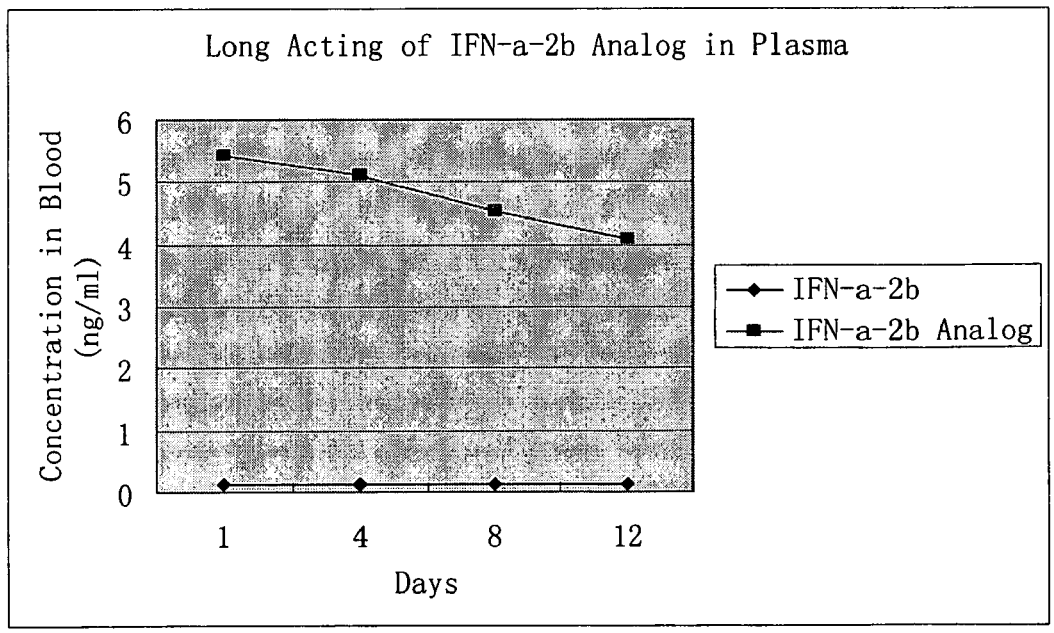

US 7,572,437 B2

LONG ACTING HUMAN INTERFERON ANALOGS

CROSS REFERENCE TO RELATED APPLICATIONS

This application claims the priority benefit of U.S. Provisional Application Ser. No. 60/483,984 filed Jun. 30, 2003, which is hereby incorporated herein by reference in its entirety. This application is also a continuation-in-part of U.S. patent application Ser. No. 10/609,346, filed on Jun. 26, 2003, now U.S. Pat. No. 7,244,833 B2, which claims the benefit under 35 USC 119(e) of U.S. Patent Provisional Application Ser. No. 60/392,948 filed on Jul. 1, 2002.

BACKGROUND OF THE INVENTION

1. Field of the Invention

This invention relates to the manufacture and use of recombinant albumin fusion proteins to make human interferon analogs. The novel interferon analogs have the same functions with interferon in bio-assays, in vitro or in vivo. These long acting recombinant interferon analogs that are particularly expressed in yeast can largely improve interferon's therapeutic function.

2. Description of Related Art

1. Albumin

Albumin is a soluble, monomeric protein that comprises about one-half of the blood serum protein. Albumin functions primarily as a carrier protein for steroids, fatty acids, and thyroid hormones and plays a role in stabilizing extracellular fluid volume. Mutations in this gene on chromosome 4 result in various anomalous proteins. Albumin is a globular unglycosylated serum protein of molecular weight 65,000. The human albumin gene is 16,961 nucleotides long from the putative 'cap' site to the first poly(A) addition site. It splits into 15 exons which are symmetrically placed within the 3 domains that are thought to have arisen by triplication of a single primordial domain. Albumin is synthesized in the liver as pre-pro-albumin which has an N-terminal peptide that is removed before the nascent protein is released from the rough endoplasmic reticulum. The product, proalbumin, is in turn cleaved in the Golgi vesicles to produce the secreted albumin. HSA has 35 cysteines; in blood this protein monomer has 17-disulfide linkage (Brown, J. R. "Albumin structure, Function, and Uses" Pergamon, N.Y., 1977). HSA is misfolded when produced intracellularly in yeast without its amino terminal secretion peptide sequence. This conclusion is based on its insolubility, loss of great than 90% of its antigenicity (as compared to human-derived HSA), and formation of large protein aggregates. At present albumin for clinical use is produced by extraction from human blood. The production of recombinant albumin in microorganisms has been disclosed in EP 330 451 and EP 361 991.

Albumin is a stable plasma transporter function provided by any albumin variant and in particular by human albumin. HSA is highly polymorphic and more than 30 different genetic alleles have been reported (Weikamp L, R, et al., Ann. Hum. Genet., 37 219-226, 1973). The albumin molecule, whose three-dimensional structure has been characterized by X-ray diffraction (Carter D. C. et al., Science 244, 1195-1198, 1989), was chosen to provide the stable transporter function because it is the most abundant plasma protein (40 g per liter in human), it has a high plasma half-life (14-20 days in human, Waldmann T. A., in "Albumin Structure, Function and Uses", Rosenoer V. M. et al (eds), Pergamon Press, Oxford, 255-275, 1977), and above all it has the advantage of being devoid of enzymatic function, thus permitting its therapeutic utilization at high dose.

2. Interferons

Interferons are a heterogeneous family of multifunctional cytokines whose first demonstrated biological activity was the induction of cellular resistance to virus infection. Antiviral activity of interferon was the only recognized biological function of the interferons for many years. Today interferons are found many other bio-functions. Interferon's actions on cell growth and differentiation and their many immunoregulatory activities are probably of greater fundamental biological significance.

Two very distinct families of proteins are counted among the interferons. The IFN-α/β "superfamily" (also called type I IFN) encompasses a group of structurally related genes and proteins that are further subdivided into the subfamilies IFN-$α_I$, IFN-$α_{II}$, and IFN-β. The second "family" consists of a single gene encoding a single protein termed IFN-γ (also called type II IFN or immune IFN). It should be made clear at the outset that IFN-γ is structurally unrelated to the members of the IFN-α/β superfamily. The reasons for discussing IFN-α/β and IFN-γ together are largely historical. Interferon was first described by Isaacs and Lindenmann (1957) as a product of virus-infected cells capable of inducing resistance to infection with homologous or heterologous viruses. A functionally related virus inhibitory protein (today termed IFN-γ) was described by Wheelock (1965) as an "Interferon-like" substance produced by mitogen-activated T-lymphocytes. For many years the only properties that made it possible to distinguish IFN-γ from the other interferons were its lack of stability at Ph 2 (Wheelcok 1965) and distinct antigenic specificity (Youngner and Salvin 1973). Only when the sequences of the proteins and genes of the major interferons were revealed in the early 1980s did it become clear what the relationship of the different interferons is to each other. People recognize now that IFN-γ is primarily an immunoregulatory cytokine whereas the potential actions of IFN-α/β extend to a broader variety of cells and tissues.

Members of the IFN-α/β superfamily represent the classical interferons. The first clear indication of the heterogeneity of the type I interferon proteins came from studies showing that interferons derived from human leukocytes and fibroblasts are antigenically distinct (Havell et al. 1975). Eventually leukocyte and fibroblast interferons were designated IFN-α and -β, respectively (COMMITTEE ON INTERFERON NOMENCLATURE 1980). Most of the information on interferon structure has been derived from gene cloning studies. At least 24 nonallelic human IFN-α genes and pseudogenes have been identified. They can be divided into two distinct subfamilies, termed IFN-$α_I$ and -$α_{II}$ (Weissmann and Weber 1986). The IFN-$α_I$ subfamily potentially functional genes and several pseudogenes. The IFN-$α_{II}$ subfamily is known to comprise only one functional gene and five or six nonallelic pseudogenes. IFN-αI genes encode mature proteins consisting of 165-166 amino acids; IFN-αII gene encodes a mature protein 172 amino acids long. All of the genes encode N-terminal secretive signal peptide presequences (generally 23 residues long) which are removed by proteolytic cleavage before the release of the mature interferon molecule from the cell. While it is clear that a high degree of homology is found among all human IFN-α genes and proteins, the IFN-$α_{II}$ sequences have diverged significantly from the -$α_I$ sequences, warranting their classification into a separate subfamily (Capon et al. 1985). In fact, it has been suggested that the IFN-$\alpha_{II}$ subfamily be named IFN-ω (Adolf 1987).

IFN-α forms vary in molecular mass between 19 and 26 kDa and are produced by monocytes/macrophages, lymphoblastoid cells, fibroblasts, and a number of different cell types following induction by viruses, nucleic acids, glucocorticoid hormones, and low-molecular weight substances. The effects of IFN-α are wide ranging and include potent anti-viral and anti-parasitic activity. In addition, IFN-α has anti-proliferative effects on certain tumor cells. Human IFN-α species lack potential N-glycosylation sites and most members of the IFN-α subfamilies in their native state are not glycosylated (Pestka 1983). Several natural human IFN-α proteins have been purified to homogeneity. They were shown to range in their apparent molecular weights from 16000 to 21000 (Rubinstein et al. 1981). The reason for these large differences in the apparent molecular weights has not been fully explained.

A single gene for human IFN-β encodes a 166-residue-long mature protein. Homology between IFN-β and members of the IFN-$\alpha_I$ subfamily is about 25-30% at the amino acid level and about 45% in the coding sequences at the nucleotide level (Taniguchi et al. 1980). In addition, there is also extensive homology in the 5'nucleotide flanking regions which contain transcriptional promoter and enhancer sequences, reflecting the fact that IFN-α and -β genes are often coordinately induced (Degrave et al. 1981).

Interferons represent an important class of biopharmaceutical products, which have a proven track record in the treatment of a variety of medical conditions, including the treatment of certain autoimmune diseases, the treatment of particular cancers, and the enhancement of the immune response against infectious agents. To date, five types of interferons have been found in humans: interferon-alpha, interferon-beta, interferon-gamma, interferon-omega and a new form of human and murine interferon, "interferon-.epsilon.," which have applications in diagnosis and therapy.

Interferon is used for treatment of Hepatitis C, B, and broad range of cancers, such as chronic myelogenous leukemia. Hepatitis C is an inflammation of the liver caused by hepatitis C virus infection. The HCV is most common chronic blood-borne disease in China (almost 80 millions HCV carrier) and USA (almost 4 millions HCV carriers), which causes 1 million people death worldwide per year. Chronic hepatitis B is an inflammation of the liver caused by HBV. The HBV infection can be developed into liver cancer and cirrhosis. 500 million people are infected by HBV in worldwide.

Production of IFN-α/β during virus infections is generally beneficial as it serves to limit the spread of virus and promote recovery (Gresser et al. 1976). In the past few years several types of interferon preparations have been licensed for clinical use. In the United States *E. coli*-derived recombinant human IFN-α 2 (IFN-α-2a) and IFN-α A (IFN-α-2b) have been approved for use in the treatment of hairy cell leukemia. IFN-α 2 and IFN-α A are both members of the IFN-$\alpha_I$ subfamily and they differ from each other in a single amino acid in position 23 (Arg in α2 and Lys in α A). One of the preparations has also been approved for the treatment of condylomata acuminata. Other interferon preparations also have been approved for clinical use in some countries, e.g., a natural mixture of several IFN-α subtypes produced in the Namalwa line of human lymphoblastoid cells or natural human IFN-β produced in cultured fibroblasts. The approved use of these interferon preparations some countries includes chronic active hepatitis B, acute viral encephalitides, and nasopharyngeal carcinoma. A preparation of *E. Coli*-derived recombinant human IFN-γ has been approved for therapeutic use in rheumatoid arthritis in the German Federal Republic. Approved and experimental therapeutic applications of interferons have been extensively covered in a volume devoted to this topic (Finter and Oldham 1985). Interferon-beta, preferably in low doses, is used for stimulation of erythropoiesis in disorders characterized by lack of maturation of progenitor blood cells to red cells, (Michalevicz, U.S. Pat. No. 5,104,653)

Novel polypeptide produced by *E. coli* transformed with a newly isolated and characterized human IFN-.alpha and the gene is described. The polypeptide exhibits interferon activities such as antiviral activity, cell growth regulation, and regulation of production of cell-produced substances. Those novel interferon are named as Interferon-α-67, by Innis, in U.S. Pat. No. 5,098,703; Interferon-.alpha.54, in U.S. Pat. No. 4,975,276, and Interferon-.alpha.61, in U.S. Pat. No. 4,973,479.

Therapeutically synergistic mixtures of purified gamma interferon and purified interleukin-2 are provided for treatment of tumor-bearing hosts. Preferably, the gamma interferon and interleukin-2 are obtained from recombinant cell synthesis (Palladino U.S. Pat. No. 5,082,658).

The invention provides fusion proteins comprising an N-terminal region derived from an interferon-tau (IFN-.tau.) polypeptide and a C-terminal region derived from another type I interferon polypeptide, such as IFN-.alpha. or IFN-.beta. The fusion proteins exhibit reduced cytotoxicity compared to the corresponding unmodified type I interferons. Johnson, et al. U.S. Pat. No. 6,174,996 is the only patent that mentions how to make an interferon fusion protein.

A method that comprises administering a PEG.sub.12000-IFN alpha conjugate to an individual afflicted with a viral infection susceptible of treatment with interferon alpha, preferably chronic hepatitis C, is disclosed. Glue et al. U.S. Pat. No. 5,908,621 is a patent mentions how to make a long acting or slow release form interferons. Shechter et al., (Proc. Natl. Acad. Sci. USA. 2001 Jan. 30; 98 (3): 1212-1217) reported the method to prolong the half-life of human interferon-α2 in circulation by covalently linked seven moieties of 2-sulfo-9-fluorenylmethoxycarbonyl (FMS) to the amino groups of human interferon-α2.

There is an invention that features a novel hybrid interferon species that comprises a chain of 161 and/or 162 amino acids. The hybrid is novel not only because its new structure, but also for the reason that the hybrid comprises a shortened or truncated segment of alpha interferon. Hence, an entirely new interferon species which does not occur in nature is reported by Leibowitz et al. in U.S. Pat. No. 4,892,743.

Chang et al. in U.S. Pat. No. 5,723,125 patent disclosed a hybrid recombinant protein consisting of human interferon, preferably interferon-.alpha. (IFN.alpha.), and human immunoglobulin Fc fragment, preferably .gamma.4 chain. These two protein fragments are joined by a peptide linker comprising the sequence Gly Gly Ser Gly Gly Ser Gly Gly Gly Gly Ser Gly Gly Gly Gly Ser. This method makes an interferon-α fusion protein.

Kriegler, et al. in U.S. Pat. No. 5,324,655 patent reported a virion expression system for a desired protein packaged in an envelope derived from a retrovirus useful in administering proteins which cross cell membranes in order to serve their function. Preferred virions are those that carry an RNA sequence that encodes cytokines or lymphokines, and includes IL-2, multiple drug resistance protein, and TNF. Particularly disclosed is a DNA construct in which a gene encoding tumor necrosis factor (TNF) is directly linked to DNA encoding a human gamma-interferon signal peptide.

There are some research paper reported that the combination use of interferons could bring some beneficial to patients such as Trotta in U.S. Pat. No. 5,190,751 patent reported the human leukemia T-cells and B-cells are inhibited from proliferating by treatment with a combination of recombinant human alpha and gamma interferons, either simultaneously or sequentially, and the alpha interferon is preferably recombinant human alfa-2b interferon.

A common feature for any of these administration modes, however, is rapid inactivation of IFN-α in body fluids and in various tissues (O'Kelly, et al., 1985. *Proc. Soc. Exp. Biol. Med.* 178, 407-411). This in turn leads to the disappearance of the cytokine from the plasma within several hours after administration (Rostaing, et al., 1998, *J. Am. Soc. Nephrol.* 9, 2344-2348). Unlike many other administered protein drugs, the major route of IFN-α elimination in vivo takes place in the circulatory system through proteolysis and inactivation by serum proteases. Therefore, long acting of interferon is needed in treatment of patients with viral infection or cancers in clinical trials.

DETAILED DESCRIPTION OF THE INVENTION

The present invention provides innovative compositions, kits and methods for making long acting Interferon analogs in vivo that promote protection of virus infection and stimulate immune response to enhance general health or treat diseases or undesirable conditions.

In general, recombinant analog of interferon, fusion proteins of human serum albumin (HSA) and an Interferon, are provided in order to circumvent problems associated with conventional therapy using the Interferon protein itself. Generally, compared with the Interferon protein alone, the inventive Interferon analogs of the present invention possess the following advantages: 1) being capable of stimulating immune response of human body while viral infection happen; 2) allowing a slower release of the HSA-Interferon fusion in the body to maximize the therapeutic effects of the Interferon, and/or 3) reducing potential side effects or toxicity associated with administration of Interferon alone.

The present invention also provides a method for treating a patient with an Interferon in need thereof. In one embodiment, the method comprises administering a pharmaceutical formulation comprising an analog of Interferon to the patient in a therapeutically effective amount. The formulation may contain any pharmaceutically acceptable excipient and agents that stabilizes the HSA/IFN fusion protein. The formulation may further comprises natural or recombinant human serum albumin and/or another, different HSA/IFN fusion protein.

In addition, the present invention also provides efficient, cost-effective large scale production of these recombinant proteins in yeast. In particular, fusion proteins of HSA with each of human Interferon-α-2a, Interferon-α-2b, and Interferon-ω have been expressed in a yeast strain of *Pichia pastoria* and shown to have superior stability in storage and in plasma with the same bio-function in cell protection experiments in vitro.

1. HSA/IFN Fusion Proteins

In one aspect of the invention, isolated polynucleotides are provided that encode fusion proteins formed between HSA and an Interferon, i.e., HSA/IFN fusion. It should be noted that other types of albumin can also be employed to produce a fusion protein with an Interferon of the present invention.

The Interferon may include any protein that belongs to the family of Interferon. In a particular embodiment, the Interferon is a nature active cytokine produced by a virus infection. Examples of such a Interferon are described in Vilcek (1991) "Interferons", in "Peptide Growth Factors and Their Receptors II", edited by Sporn and Roberts, Spring-Verlag Heidelberg, New York Inc., USA. pp 3-38 which is incorporated herein by reference in its entirety.

Specific examples of the Interferon include, but are not limited to, Interferon alpha-1 (IFNA-1), alpha-2 (IFNA-2), alpha-4 (IFNA-4), alpha-5 (IFNA-5), alpha-6 (IFNA-6), alpha-7 (IFNA-7), alpha-8 (IFNA-8), alpha-10 (IFNA-10), alpha-12 (IFNA-12), alpha-13 (IFNA-13), alpha-14 (IFNA-14), alpha-16 (IFNA-16), alpha-17 (IFNA-17), alpha-21 (IFNA21); Interferon-beta-1 (IFNB-1), interferon-beta-2 (IFNB-2, also be named as interleukin-6, IL-6); Interferon-lambda-1 (Interleukin-29), Interferon-lambda-2 (Interleukin-28A); and/or Interferon-epsilon.

Three distinct Interferon analogs have been made and well characterized: HSA-INF-α-2a, HSA-INF-α-2b, HSA-INF-β, HSA-INF-ω, and HSA-INF-γ. Other interferons or interferon family members are made by same techniques.

The Interferon may be linked directly to the N-terminus or C-terminus of HSA to form an analog. Optionally, there is a peptide linker (L) that links HSA and Interferon to form the fusion proteins HSA-L-IFN, or IFN-L-HSA. The length of peptide is usually between 2-100 aa (preferably between 5-50 aa, and most preferably between 14-30 aa). The peptide linker may be a flexible linker that minimizes steric hindrance imposed by the bulk HA protein on interferon, such as a $(G_4S)_{3-4}$ linker. The linker addition may be good for interferon binds to its receptor. The addition of a linker to the in between of HSA and a therapeutic protein needs more work to validated the damage which may cause to when the fusion protein to be used as a therapeutic treatment on human. Because of the 6 amino acids and up peptides can have own immunity in human body. Preferably, there is no linker in the peptide of a human interferon analog. More preferably, there is no linker in the peptide of a long acting of HSA fusion protein drug.

The fusion protein may be a secret protein, which binds to a specific antibody of human albumin, and optionally, binds to a specific antibody of the interferon in this fusion protein.

In one embodiment, an isolated polynucleotide is provided that encodes a human serum albumin-interferon-α fusion protein (HSA-IFN-α-1β). The polynucleotide comprises a nucleotide sequence at least 90% identical to SEQ ID NO. 1 (FIG. 1). Preferably, the polynucleotide comprises a nucleotide sequence at least 95% identical to SEQ ID NO. 1. Preferably, the polynucleotide encodes an amino acid sequence comprising SEQ ID NO. 2 [HSA-IFN-α-1b].

In one embodiment, an isolated polynucleotide is provided that encodes a human serum albumin-interferon-α-2b fusion protein (HSA-IFN-α-2b). The polynucleotide comprises a nucleotide sequence at least 90% identical to SEQ ID NO. 3. Preferably, the polynucleotide comprises a nucleotide sequence at least 95% identical to SEQ ID NO. 3. Preferably, the polynucleotide encodes an amino acid sequence comprising SEQ ID NO. 4 [HSA-IFN-α-2b].

In another embodiment, an isolated polynucleotide is provided that encodes a human serum albumin-Interferon-β fusion protein (HSA-IFN-β). The polynucleotide comprises a nucleotide sequence at least 90% identical to SEQ ID NO. 5. Preferably, the polynucleotide comprises a nucleotide sequence at least 95% identical to SEQ ID NO. 5. Preferably, the polynucleotide encodes an amino acid sequence comprising SEQ ID NO. 6. [HSA-IFN-β].

In yet another embodiment, an isolated polynucleotide is provided that encodes a human serum albumin-Interferon-ω fusion protein (HSA-IFN-ω). The polynucleotide comprises a nucleotide sequence at least 90% identical to SEQ ID NO. 7. Preferably, the polynucleotide comprises a nucleotide sequence at least 95% identical to SEQ ID NO. 7. Preferably, the polynucleotide encodes an amino acid sequence comprising SEQ ID NO. 8 [HSA-IFN-ω].

In yet another embodiment, an isolated polynucleotide is provided that encodes a human serum albumin-Interferon-γ fusion protein (HSA-IFN-γ). The polynucleotide comprises a nucleotide sequence at least 90% identical to SEQ ID NO. 9. Preferably, the polynucleotide comprises a nucleotide sequence at least 95% identical to SEQ ID NO. 9. Preferably, the polynucleotide encodes an amino acid sequence comprising SEQ ID NO. 10 [HSA-IFN-γ].

In yet another embodiment, an isolated polynucleotide is provided that encodes a human serum albumin-Interferon fusion protein (HSA-IFN). The polynucleotide comprises a nucleotide sequence at least 90% identical to SEQ ID NO. 11. Preferably, the polynucleotide comprises a nucleotide sequence at least 95% identical to SEQ ID NO. 11. Preferably, the polynucleotide encodes an amino acid sequence comprising SEQ ID NO. 12 [HSA].

Optionally, the polynucleotide further comprises a nucleotide sequence at least 90% identical to SEQ ID NOs. 13, 15, 17, 19, or 21. Preferably, the polynucleotide further comprises a nucleotide sequence encoding an amino acid sequence comprising SEQ ID NOs. 14, 16, 18, 20, or 22.

According to the embodiment, the Interferon may be selected from the group consisting, such as, but not limited, Interferon alpha-1 (IFNA-1), alpha-2 (IFNA-2), alpha-4 (IFNA-4), alpha-5 (IFNA-5), alpha-6 (IFNA-6), alpha-7 (IFNA-7), alpha-8 (IFNA-8), alpha-10 (IFNA-10), alpha-12 (IFNA-12), alpha-13 (IFNA-13), alpha-14 (IFNA-14), alpha-16 (IFNA-16), alpha-17 (IFNA-17), alpha-21 (IFNA21); Interferon-beta-1 (IFNB-1), interferon-beta-2 (IFNB-2, also be named as interleukin-6, IL-6); Interferon-lambda-1 (Interleukin-29), Interferon-lambda-2 (Interleukin-28A); and/or Interferon-epsilon.

The above-described polynucleotide with a sequence having a certain degree of sequence identity, for example at least 95% "identical" to a reference nucleotide sequence encoding a HSA/IFN fusion protein, is intended that the polynucleotide sequence is identical to the reference sequence except that the polynucleotide sequence may include up to five point mutations per each 100 nucleotides of the reference nucleotide sequence encoding the HSA/IFN fusion protein. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the polynucleotide sequence encoding a HSA/IFN fusion protein can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

When stored at ambient temperature or a lower temperature, the fusion protein of HSA and IFN may have a shelf-life 2 times longer, preferably 4 times longer, more preferably 6 times, and most preferably 10 times, longer than that of the IFN alone stored under the same condition.

The present invention involves the utilization of albumin as a vehicle to carry a therapeutic protein such as an IFN in the treatment of certain diseases such as cancers, or people in need of an increased blood cell proliferation in order to increase the blood cell numbers. The fusion protein of the present invention may be administered to a mammal, preferably a human, via a variety of routes, including but not limited to, orally, parenterally, intraperitoneally, intravenously, intraarterially, topically, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The analogs of Interferon, HSA-IFN, may also be delivered to the host locally (e.g., via stents or cathetors) and/or in a timed-release manner. In a particular embodiment, the fusion protein is delivered parenterally via injection.

When delivered in vivo to an animal, the fusion protein of HSA and IFN, Interferon analogs, may have a plasma half-life 2-10 times longer than that of the IFN alone.

The HSA/IFN fusion proteins of the present invention may also be administered in combination with a natural or recombinant human albumin, preferably a recombinant one at a therapeutically effective dose and ratio.

It is believed that after fusion with albumin, the IFN protein can have a longer shelf-life and plasma half-life, which allows cost-effective storage and transportation, as well as reduces amount and/or frequency of drug administration.

It is believed that other polypeptide form anti-virus or peptide inhibitors of virus entry cell after fusion with albumin, the peptide protein can have a longer shelf-life and plasma half-life, which allows maintaining same bio-function of peptide and gives a long acting therapeutic function. The peptides such as T20 can block the HIV virus entry of HIV targeted cells 2. Expression of Interferon Analogs in Host Organisms The polynucleotides encoding the inventive Interferon analogs, HSA/IFN fusion proteins, can be cloned by recombinant techniques into vectors which are introduced to host cells where the fusion proteins can be expressed.

Generally, host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the polynucleotides encoding HSA/IFN fusion proteins. The culture conditions, such as temperature, pH and the like, are those previously used with the host cell selected for expression, and will be apparent to the ordinarily skilled artisan.

According to the invention, a recombinant vector is provided that comprises the polynucleotide sequence encoding an HSA/IFN fusion protein. The recombinant vectors can be an expression vector for expressing the Interferon analogs, HSA fusion protein encoded by the nucleic acid, HSA-IFN, HSA-L-IFN, or IFN-L-HSA in a host organism. The host organism includes, but is not limited to, mammalian (e.g., human, monkey, mouse, rabbit, etc.), fish, insect, plant, yeast, and bacterium.

Expression of the polynucleotide encoding an HSA/IFN fusion protein is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, a tetracycline or tetracycline-like inducible promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the polynucleotide encoding an HSA/IFN fusion protein.

Also according to the invention, a recombinant cell is provided that is capable of expressing comprises the polynucleotide sequence encoding an HSA/IFN fusion protein. The recombinant cell may constitutively or be induced in the presence or absence of an agent to express Interferon analog, HSA fusion protein, encoded by the nucleic acid, HSA-IFN, HSA-L-IFN, or IFN-L-HSA in a host organism. The type of the recombinant cell includes, but is not limited to, mammalian (e.g., human, monkey, mouse, rabbit, etc.), fish, insect, plant, yeast, and bacterial cell.

In a preferred embodiment, the host organism belongs to a genus of yeast such as *Saccharomyces* (e.g., *S. cerevisiae*), *Pichia, Kluyveromyces, Hansenula, Torulaspora,* and *Schinosaccharomyces*. In a more preferred embodiment, the host organism is *Pichia pastoris*. In a particular embodiment, the recombinant vector is a pPICZ A, pPICZ B, or pPICZ C.

Depending upon the host employed in a recombinant process for producing the fusion proteins, the fusion proteins of the present invention may be glycosylated or non-glycosylated. Preferably, when expressed in a host organism, the fusion protein of HSA and IFN may be glycosylated to substantially the same extent as that when expressed in mammalian cells such as Chinese hamster ovarian (CHO) cells, or as that when expressed in *Pichia pastoris*.

As indicated above, the albumin fusion proteins of the present invention are substantially preferably proteomic and can therefore be generated by the techniques of genetic engineering. The preferred way to obtain these fusion proteins is by the culture of cells transformed, transfected, or infected by vectors expressing the fusion protein. In particular, expression vectors capable of transforming yeasts, especially of the genus *Pichia*, for the secretion of proteins will be used.

It is particularly advantageous to express the HSA/IFN fusion protein in yeast. Such an expression system allows for production of high quantities of the fusion protein in a mature form, which is secreted into the culture medium, thus facilitating purification.

The development of yeast genetic engineering has been made possible the expression of heterologous genes and the secretion of their protein products from yeast. The advantages of protein secretion (export) of yeast include, but not limited to, high expression level, soluble protein, corrected folding, easy to scale-up and easy for purification.

HSA/IFN fusion proteins, the Interferon analogs, can be secreted into the media of yeast via an albumin natural secretion signal. The polypeptide sequence of HSA fusion protein can be preceded by a signal sequence which serves to direct the proteins into the secrete pathway. In a preferred embodiment the prepro-sequence of human albumin is used to secrete the fusion protein out of yeast cells into the culture medium. Other secrete signal peptides, such as the native *Saccharomyces cerevisiae* α-factor secretion signal, can also be used to make fusion protein of the present invention.

Yeast-expressed HSA is soluble and appears to have the same disulfide linkages as the human-blood derived counterpart. If used in a large scale production, which may be potentially used in gram amounts in humans, a recombinant HSA will require a close identity with the natural HSA product. Secreting the HSA/IFN fusion protein into the growth media of yeast, which is via prepro-amino-terminal processing (no initiator methionine residue), also circumvents the problems associated with preparing yeast extracts, such as the resistance of yeast cells to lysis. In addition, the purity of the product can be increased by placing the product in an environment in which 0.5-1.0% of total yeast proteins is included and the lacks toxic proteins that would contaminate the product.

In a preferred embodiment, a particular species of yeast *Pichia pastoris* is used in the system for expressing HSA/IFN fusions of the present invention. *Pichia pastoris* was developed into an expression system by scientists at Salk Institute Biotechnology/Industry Association (SIBA) and Phillips Petroleum for high-level expression of recombinant proteins. The techniques related to *Pichia* are taught in, for example, U.S. Pat. Nos. 4,683,293, 4,808,537, and 4,857,467.

There are some advantages of using yeast *Pichia pastoris* to express HSA and HSA fusion proteins than using other systems. *Pichia pastoris* is a species of yeast genus, *Pichia*. *Pichia* has many advantages of higher eukaryotic expression systems such as protein processing, protein folding, and post-translational modification, while it is as easy to manipulate as *E. coli* or *Saccharomyces cerevisiae*. It is faster, easier, and less expensive to use than other eukaryotic expression systems such as baculovirus or mammalian tissue culture, and generally gives higher expression levels. *Pichia* has an additional advantage which gives 10-100 fold higher heterogonous protein expression levels. Those features make *Pichia* a very useful protein expression system.

Due to the similarity between *Pichia* and *Saccharomyces*, many techniques developed for *Saccharomyces* may be applied to *Pichia*. These include transformation by complementation, gene disruption, and gene replacement. In addition, the genetic nomenclature used for Sac has been applied to *Pichia*. For example, histidinol dehydrogenase is encoded by HIS4 gene in both Sac and *Pichia*. *Pichia* as a methylotrophic yeast is capable of metabolizing methanol as its sole carbon source. The first step in the metabolism of methanol is oxidation of methanol to formaldehyde using molecular oxygen by the enzyme called alcohol oxidase. In addition to formaldehyde, this reaction also generates hydrogen peroxide. To avoid hydrogen peroxide toxicity, methanol metabolism takes place within a specialized cell organelle, called the peroxisome, which sequesters toxic by-products away from the rest of the cell. Alcohol oxidase has a poor affinity for $O_2$, and *Pichia* compensates it by generating large amounts of this enzyme. The promoter regulating the production of alcohol oxidase is the one used to drive heterogonous (HSA or HSA fused) protein expression in *Pichia*.

Compared with *Saccharomyces cerevisiae*, *Pichia* may have an advantage in glycosylation of secrete proteins because it generally does not hyper-glycosylate. Both *Saccharomyces* and *Pichia* have a majority of N-linked glycosylation of the high-mannose type; however, the length of the oligosaccharide chains that add post-translation ally to proteins in *Pichia* (average 8-14 mannose residues per side chain) is much shorter than those in *Saccharomyces* (50-150 mannose residues). Very little O-linked glycosylation has been observed in *Pichia*. In addition, *Saccharomyces* core oligosaccharide has terminal α-1,3 glycan linkages whereas *Pichia* does not. It is believed that the α-1,3 glycan linkages in glycosylated proteins produced from *Saccharomyces* are primarily responsible for the hyper-antigenic nature of those proteins that make them particularly unsuitable for therapeutic use. Although not yet proven, this is predicted to be less of a problem for glycoprotein generated in *Pichia*, because it may resemble the glycoprotein structure of higher eukaryotes. Protein expressed as a secrete form for correctly refolding and easy purification of HSA and HSA fusion proteins.

Watanabe, et al. (2001) "In vitro and in vivo properties of recombinant human serum albumin from *Pichia pastoris* purified by a method of short processing time", Pharm Res 2001 December:18(12):1775; and Kobayashi, K et al. (1998) "The development of recombinant human serum albumin" Ther Apher, November:2(4):257-62.

There are many expression systems available for expressing in *Pichia*, such as EasySelect™ *Pichia* Expression Kit from Invitrogen, Inc. On this vector, an AOX1 promoter is used to allow methanol-inducible high level expression in *Pichia* and a Zeocin™ resistance as selective market for the recombinants from the transformation. Promoters (transcription initiation region) are very important in expressing fusion proteins in this invention.

AOX1 gene promoter is very strong in yeast system, especially in *Pichia*. Two Alcohol Oxidase Proteins are coded in *Pichia* for alcohol oxidase—AOX1 and AOX2. The AOX1 gene is responsible for the vast majority of alcohol oxidase activity in the cell. Expression of the AOX1 gene is tightly regulated and induced by methanol to very high levels, typically ≧30% of the total soluble protein in cells grown with methanol as the carbon source. The AOX1 gene has been isolated and a plasmid-bone version of the AOX1 promoter is used to drive expression of the gene of interest encoding the desired heterogonous protein (Ellis et al., 1985; Koutz et al., 1989; Tschopp et al., 1987a). While AOX2 is about 97% homologous to AOX1, growth on methanol is much slower than with AOX1. This slow growth on methanol allows isolation of Mut$^s$ strains (aox1). Except for AOX1 gene promoter, other promoters can also be used to driver HSA fusion gene in yeast. They include the promoter from, but not limited to, PGK1, GAPDH, Gal1, Gal10, CYC1, PH05, TRP1, ADH1, and ADH2 genes. In this invention, we also disclose a novel method to make recombinant yeast with dual expression cassette insertions at two separated locations.

The expression plasmid can also take the form of shuttle vectors between a bacterial host such as *E. coli*, DH5a from GIBCO/Life Science and yeast. The antibiotic Zeocin are used to be a marker for HSA carrier vector in all the examples.

The expression vector that contains the polynucleotide of HSA or HSA fusion therapeutic protein is introduced into yeast according to the protocols described in the kit from Invitrogen Inc. After being selected from transformed yeast colonies, those cells that express the HSA fusion protein of interest are inoculated into appropriate selective medium and then tested for their capacity to secrete the given fusion protein into the extracellular medium. The harvest of the protein can be conducted during cell growth for continuous cultures, or at the end of the growth phase for batch cultures. The fusion proteins which are the subject of this invention are then further purified from the culture supernatant by methods which take into account the albumin purification methods and pharmacological activities.

It is noted that other expression systems may also be used to express rHSA and HSA/IFN fusion proteins, including but not limited to, *E. coli*, *B. Subtitis*, *Saccharomyces*, *Kluyveromyces*, *Hansenula*, *Candida*, *Torulopsis*, *Torulaspora*, *Schizosaccharomyces*, *Citeromyces*, *Pachysolen*, *Debaromyces*, *Metschunikowia*, *Rhodosporidium*, *Leucosporidium*, *Botryoascus*, *Sporidiobolus*, *Endomycopsis*, animals, plants, and insect cells.

3. Combination Therapy of Interferon Analogs

The present invention also provides combinations of different Interferon analogs. The specific combinations of these interferon analogs or nature interferons may be administered to a patient to stimulate multiple types of protection to viral targeted cells or to synergistically enhance proliferation of a particular cell type. In particular, a combination of human albumin fusions with different hematopoietically active cytokines is used to effectively promote proliferation of the multiple blood cells and platelets. By using a combination of HSA/IFN fusion proteins targeting the signal transduction pathways of different types of blood cells, multiple blood functional cell production, such as platelets, erythrocytes and macrophages of white cells, can be increased after administration by just one injection.

In the present invention, the albumin's plasma transporter function and the therapeutic function of the IFN are integrated into a fusion form. The presence of albumin may confer a superior stability to the IFN by resisting degradation by proteases in the blood circulation, thus significantly prolonging the plasma half life of the IFN. Due to the masking effect of a bulky albumin, different IFNs fused with albumin in the combination may impose less interference with the biological function(s) of each other than a combination of the "naked" IFNs. Furthermore, an IFN fused with albumin may be slowly released in the system over an extensive period of time, thereby reducing the toxicity associated with injection of the IFN alone in abnormally high concentrations in the body. Such a slow release mode of action of the fusion protein combination can significantly reduce the amount and/or frequency of injections of the IFN, thereby further reducing the side effects of IFNs. Such combinations that are particularly useful for stimulating multiple blood cell proliferation after or before the chemo- or radiation therapy of cancer patients who are tolerance for frequent, high dose injection of IFN are seriously compromised.

According to the present invention, HSA fusion protein with this type of IFN may remove above limitations by slowly releasing the drug into the patient's system. In addition, such fusion proteins may be combined with a relatively higher amount of albumin to further reduce the impact resulted from directly injecting the drug into the blood which causes a strong, adverse reaction of the central nervous system.

It is also known that "naked" cytokines (i.e., cytokines not fused to another protein such as HSA) are quite unstable when stored and have a short plasma half-life. Clearly, a therapeutic protein with such a weak stability in vivo constitutes a major handicap. In effect, repeated injections of the product, which are costly and inconvenient for patient, or an administration of product by perfusion, become necessary to attain an efficient concentration in plasma. Due to its extended plasma half and enhanced stability, the HSA/IFN fusion proteins of the present invention and their combinations, e.g., HSA fusions with Interferon-α, interferon-β, interferon-ω and interferon-γ, can be used to stimulate the production of antivirus peptides in plasma of humans.

In one embodiment, HSA/IFN-α fusion may be combined with HSA/IFN-γ fusion and the resulting combination may be administered to a patient with a virus infection to simultaneously stimulate secretion of antiviral peptides. For example, cancer patients may be injected with a combination of HSA/IFN-α and HSA/IFN-γ fusion proteins, before or after, a viral infection to avoid the damages of cells and organs. The Interferon-α will promoter the fight with virus and Interferon-g will fight inhibit the cancer cell proliferation.

Alternatively, an HSA/IFN fusion may be co-administered with a different HSA/IFN fusion simultaneously or sequentially to a patient in need thereof. This combination therapy may confer synergistic therapeutic effects on the patients. In one embodiment, the method is provided, comprising: administering a first pharmaceutical formulation comprising a first fusion protein of HSA and a first IFN to the patient in a therapeutically effective amount; and administering to the patient a second pharmaceutical formulation comprising a second fusion protein of HSA and a second IFN to the patient in a therapeutically effective amount. Such a combination therapy may confer synergistic therapeutic effects on the patient.

For example, HSA-IFN-α-2b fusion protein may be administered to the patient first, followed by administration of HSA-IFN-γ, HSA-IFN-ω and/or HSA-IFN-β at therapeutically effective doses and ratios to inhibit cancer cell proliferation of different and to induce antiviral peptide secretion from cells.

The present invention further provides a kit for use in the combination therapy described above. The kit comprises: a first fusion protein of HSA and a first IFN, and a second fusion protein of HSA and a second IFN. The first and second IFNs may be the same or different. For example, the first IFN is IFN-α-2b and the second IFN is Interferon-γ; the first IFN is Interferon-ω and the second IFN is Interferon-γ; or the first IFN is Interferon-β and the second IFN is Interferon-γ.

The HSA/IFN fusion proteins and their combinations thereof may be used to treat a wide variety of diseases, including but not limited to, the viral infection, such HAV, HBV, HCV, HPV, SARS virus, and/or HIV infection, tumors, cancers, renal failure, and tissue/organ transplantation. These fusion proteins are preferred not to contain non-human sequences that may elicit adverse immunogenicity in the patient. Interferon analogs are including but not limited to Interferon alpha-1 (IFNA-1), alpha-2 (IFNA-2), alpha-4 (IFNA-4), alpha-5 (IFNA-5), alpha-6 (IFNA-6), alpha-7 (IFNA-7), alpha-8 (IFNA-8), alpha-10 (IFNA-10), alpha-12 (IFNA-12), alpha-13 (IFNA-13), alpha-14 (IFNA-14), alpha-16 (IFNA-16), alpha-17 (IFNA-17), alpha-21 (IFNA21); Interferon-beta-1 (IFNB-1), interferon-beta-2 (IFNB-2, also be named as interleukin-6, IL-6); Interferon-lambda-1 (Interleukin-29), Interferon-lambda-2 (Interleukin-28A); and/or Interferon-epsilon.

BRIEF DESCRIPTION OF THE FIGURES

FIG. 1 shows nucleotide and amino acid sequences of embodiments of Analogs of Interferon, HSA, and examples of individual IFNs.

FIG. 6 shows the results of a stability test of Interferon analog proteins under different temperature and its cell viral protection activity. A), 37° C.; B), 50° C.

FIG. 7 shows the long acting effects in vivo test of analog interferon, HSA-IFNs, in animal plasma, as compared with those when Interferon Analog or IFN were administered. A), 1-24 hrs; B), 1-12 days.

EXAMPLES

1. General Molecular Cloning Techniques

Figure 2:
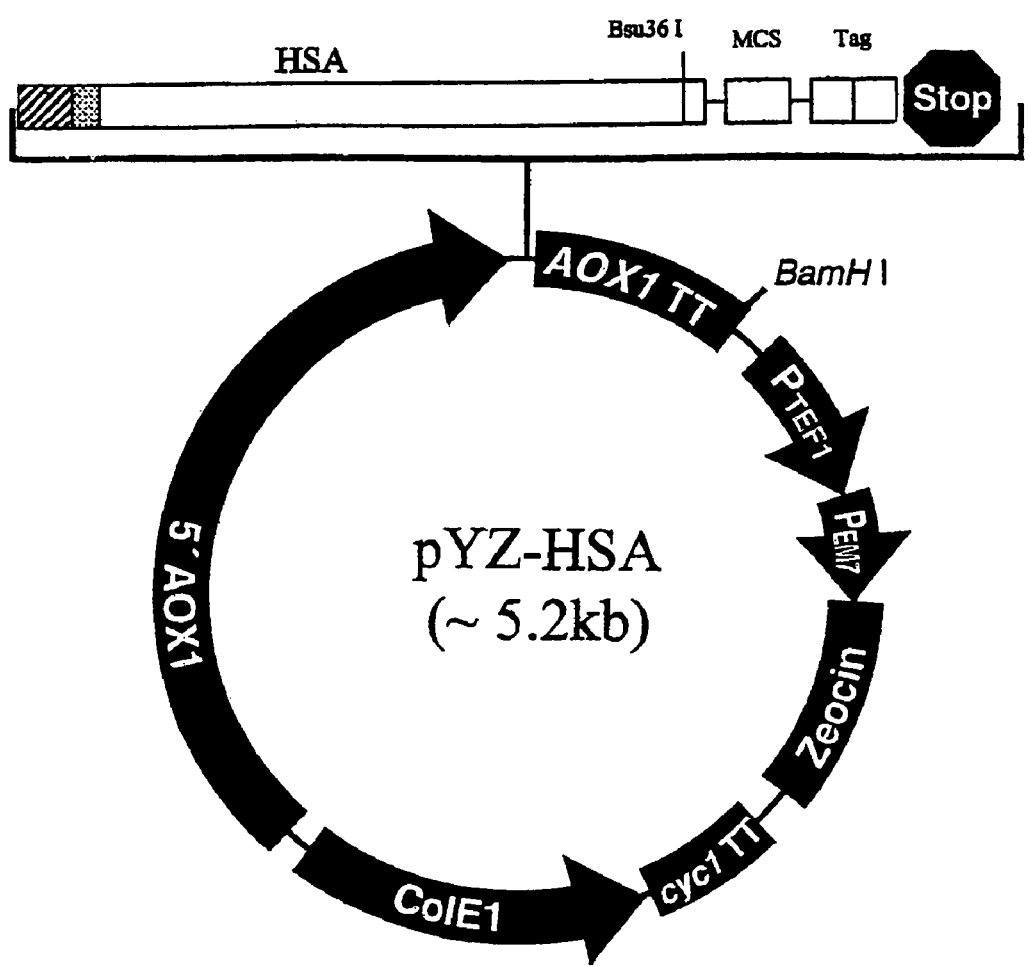
FIG. 2 illustrates a plasmid DNA vector contains the HSA sequence and as a backbone vector for making Interferon analogs, HSA-IFN fusion proteins.

The classic methods of molecular cloning that include DNA preparative extractions, agarose and polyacrylamide electrophoresis, plasmid DNA purification by column or from gel, DNA fragment ligations, and restriction digestion are described in detail in Maniatis T. et al., "Molecular cloning, a Laboratory Manual", Cold Spring Harbor laboratory, Cold Spring Harbor, N.Y., 1982 and will not be reiterated here.

Polymerase Chain Reaction (PCR) used through out all the examples is described by Saiki, R. K. et al, Science 230:1350-1354, 1985 and is carried out on a DNA thermal cycler (Perkin Elmer) according to the manufacturer's specification. DNA sequencing was performed by using standard facilities and following the method developed by Sanger et al., Proc. Natl. Acad. Sci. USA, 74:5463-5467, 1977. Oligonucleotides were synthesized by commercial facilities.

Transformation of $E.\ coli$ was done by using DH5α competent cells from GIBCO/BRL. Qiagen plasmid DNA purification columns were used in the purification of plasmid DNAs. The transformation of yeast was carried out by electroporation following the instruction provided by the manufacturer or according to the manual of EasySelect™ Pichia Expression Kit (Invitrogen Inc). All yeast stains used in the examples are members of the family of Pichia, and in particular, the strain of Pichia pastoris (supplied by Invitrogen).

2. Construction of a Backbone Vector Expressing Human Serum Albumin

A total RNA isolated from human fetal liver was used in a reverse transcription polymerase chain reaction (RT-PCR) to generate the polynucleotide encoding human serum albumin. Briefly, 5 μg of RNA was reverse transcribed by adding a poly(T)$_{18+N}$ primer and the SuperScript™ II RNase H⁻ reverse transcriptase (GIBCO/BRL) to make the complementary first strand of cDNA. The reaction was incubated at 45° C. for 20 minutes, then at 55° C. for 40 minutes.

The primers for cloning human serum albumin (HSA) are the following:

```
SEQ ID No. 23:
5'-GAATTCATGAAGTGGGTAACCTTTATTTCC-3'
and

SEQ ID No. 24:
5'-GAATTCTTATAAGCCTAAGGCAGCTTGACTTGC-3'.
```

These primers were designed based on the HSA sequence published by GenBank (Access# V00494). Two EcoR I (underline of primers) sites were created at the 5' end and 3' end for sub-cloning into an expression vector. After inactivating the reverse transcriptase at 94° C. for 4 minutes, the DNA encoding of HSA was further amplified by Taq DNA PCR (Perkin Elmer) with 35 cycles of 94° C./30 seconds and 58° C./30 seconds and 72° C./2 minutes 30 second, followed by a 72° C./10 minutes incubation. The PCR product (1842 base pairs) was confirmed by 1% agarose gel electrophoresis. The product was subcloned into a pCR II TA cloning vector from Invitrogen. DNA sequencing confirmed that the plasmid DNA contained an insert whose polynucleotide sequence matches the DNA sequence published in GenBank (Access# V00494). FIG. 1, Seq ID No. 11 is a polynucleotide DNA sequence and Seq ID No 12 is the protein amino acid sequence of human serum albumin.

After restriction digestion of the PCR product with EcoR I, the gel purified HSA DNA fragment was inserted into the EcoR I site of a pPICZ-A or pGAPZ-A vector (provided by Invitrogen) or a new vector, pYH, modified by Zailin YU. After transformation of bacteria DH5α cells with this vector encoding HSA, a colony was selected from a low salt LB-agar plate contains 25 µg/ml Zeocin. The direction of the insert was confirmed by restriction enzyme double digestion of plasmid DNA by Xho I/Nde I. The constructs were designated as pYZ-HSA (Y: yeast vector; Z: Zeocin resistant) driven by AOX1 or GAP promoter; or pYH-HSA (Y: yeast vector, Histidine resistant) driven by AOX1 or GAP (GAPDH) promoter and its physical maps are shown in FIG. 2.

There are some advantages associated with the vector constructed above. 1) It confers resistance to the antibiotic Zeocin. Zeocin is isolated from *Streptomyces* and is structurally related to bleomycin/phleomycin-type antibiotics. Antibiotics in the family of bleomycin/phleomycin are broad spectrum antibiotics that act as strong antibacterial and anti-tumor drugs. They show strong toxicity against bacteria, fungi (including yeast), plants, and mammalian cells. However, Zeocin is not as toxic as bleomycin on fungi. A single antibiotic Zeocin could be used in selecting the recombinants in both bacteria and in yeast. Further, there are multiple cloning sites at the 3' end of HSA for conveniently subcloning an IFN protein in frame to encode a HSA-IFN. 2) A myc epitope sequence and a polyhistidine tag can be fused to the C-terminal of the expressed fusion protein for easy detection and/or purification by using commercially available antibodies against myc or polyhistidine tags. 3) AOX1 promoter or GAP promoter could be used which gives more choice for convenient expression of HSA/IFN. The GAP promoter is a no methanol inducer. By using of GAP promoter than AOX promoter, the industry scale level (1,000 Kg) fermentation would be safer with no use of methanol as an additive to induce the expression. 4) A dual expression cassette (promoter, to be expressed gene and resistant gene) from two vectors could be directly inserted with controlling into same yeast strain to make recombinant yeast for higher expression. Two vectors with promoter and insert, same or not, could be transformed into a yeast strain, pYZ-HSA, will directly insert at AOX1 gene locus with Zercin resistant, using same promoter's pYH-HSA, will directly insert at His gene location with His selection function. Vectors, pYH and pYZ as backbone vectors, were used in the construction of expression vectors for HSA fusion proteins described in the Example section.

3. Molecular Cloning of Human Interferons 3.1. Molecular Cloning of Human Interferon-α-1b Gene Human Interferon-α-1b was cloned from a total RNA preparation of human white blood cells (monocytes/macrophages and B lymphocytes) by RT-PCR method described in Example 2. The oligonucleotide primers are

```
SEQ ID NO. 25: 5'-CATATGTGTGATCTCCCTGAGACCC-3'

SEQ ID NO. 26: 5'-GGATCCTTACTTCCTCCTTAATCTTTC-3'
```

A polynucleotide having 509 base pairs (bp) was amplified from RT-PCR reaction and subcloned into pCR II TA cloning vector from Invitrogen Inc. DNA sequencing confirmed the reading frame of human Interferon-α-1b. An Nde I restriction enzyme site was created at the 5' end and a Bam HI site at the 3' end (underline). The ATG initiate start codon of Interferon-a was included in this site (underlined in SEQ ID NO. 25). The DNA sequence of human Interferon-α-1b (SEQ ID NO. 13) and its amino acid sequence (SEQ ID NO. 14) are shown in FIG. 1.

3.2. Molecular Cloning of Human Interferon-α-2a Gene

Human Interferon-α-2a was cloned from a total RNA preparation of human white blood cells (monocytes/macrophages and B lymphocytes) by RT-PCR method described in Example 2. The oligonucleotide primers are

```
SEQ ID NO. 27:   5'-CATATGGCCTTGACCTTTGCTTTAC-3'

SEQ ID NO. 28:   5'-GGATCCTCATTCCTTACTTCTTAAAC-3'
```

A polynucleotide having 579 base pairs (bp) was amplified from RT-PCR reaction and subcloned into pCR II TA cloning vector from Invitrogen Inc. DNA sequencing confirmed the reading frame of human Interferon-α-2a. An Nde I restriction enzyme site was created at the 5' end and a Bam HI site at the 3' end (underline). The ATG initiate start codon of Interferon-α was included in this site (underlined in SEQ ID NO. 27).

3.3. Molecular Cloning of Human Interferon-α-2b Gene

Human Interferon-α-2b gene has only one nucleatide different with Interferon-α-2a gene that result gives an amino acid different in position #23 (Arg in interferon-α-2a and Lys in interferon-α-2b). The interferon-α-2b gene was obtained by point mutation from cloned interferon-α-2a by a kit from Stratagene company. A paired mutation primers are used to make one nucleotide change in sequence. They are

```
SEQ ID NO. 29:
5'-TGGCACAGATGAGGAAAATCTCTCTTTTCTCCTGC-3',
and
```

```
SEQ ID NO. 30:
   5'-CAGGAGAAAAGAGAGATTTTCCTCATCTGTGCCAGC-3'.
```

The underlined nucleopeptide is the mutation point, from Interferon-α-2a, AGA (Arg) to Interferon-α-2b, AAA (Lys). The experiment was performed according to the manufacture's instruction. Mutated product in pCR II vector was sequence confirmed. The human Interferon-α-2b gene DNA sequence (SEQ ID NO. 15) and amino acid sequence (SEQ ID NO. 16) are showed in FIG. 1.

3.4. Molecular Cloning of Human Interferon-β

Primers used to clone the human Interferon-β gene from a cDNA library of human leukocyte are

```
SEQ ID NO. 31:   5'-CATATGACCAACAAGTGTCTCC-3',
and

SEQ ID NO. 32:   5'-GAATTCTCAGTTTCGGAGGTAACC-3'
```

An Nde I site created at 5'end and an EcoR I site at 3'end of Interferon-β were created. The PCR products were gel-purified and subcloned into pCR2.1 TA cloning vectors and DNA sequence was confirmed. The human interferon-β DNA sequence (SEQ ID NO. 17) and the amino acid sequence (SEQ ID NO. 18) are shown in FIG. 1.

3.5. Molecular Cloning of Human Interferon-ω

Human interferon-ω was cloned from a total RNA sample prepared from human cDNA Library of Leukocyte (White Blood Cells). The primers were:

```
SEQ ID NO.33:   5'-CATATGGCCCTCCTGTTCCCTCTAC-3',
and

SEQ ID NO. 34:   5'-GAATTCTCAAGATGAGCCCAGGTCTC-3'
```

The PCR products were gel-purified and inserted into pCR2.1 TA cloning vector and sequence confirmed. The human Interferon-ω DNA sequence (SEQ ID NO. 19) and amino acid sequence (SEQ ID NO. 20) are shown in FIG. 1.

3.6. Molecular cloning of Human Interferon-γ

Human interferon-γ was cloned from a total RNA sample prepared from human cDNA library of mitogen-activated T-lymphocytes. The primers were:

```
SEQ ID NO.35:   5'-CATATGAAATATACAAGTTATATC-3'

SEQ ID NO.36:   5'-GAATTCTTACTGGGATGCTCTTCG-3'
```

The PCR products were gel-purified and inserted into pCR2.1 TA cloning vector and sequence confirmed. The human Interferon-γ DNA sequence (SEQ ID NO. 21) and amino acid sequence (SEQ ID NO. 22) are shown in FIG. 1.

4. In Frame Fusion of HSA with Human IFN-α-1b, IFN-α-2b, IFN-β, IFN-ω or IFN-γ

Interferon analogs were made by fusion human albumin gene with interferon gene. There is a Bsu36 I site at the C'-terminus of HSA. All of the Interferons described in the Example section were fused into this site by PCR primer extension to generate a restriction enzyme site of Bsu36 I at the N-terminus of the Interferon DNA sequence. The Interferon DNA fragments were amplified by PCR and then subcloned into Bsu36 I and Xho I sites of pYZ-HSA or pYH-HSA vector which had been double digested with Bsu36 I and Xho I to linearize the plasmid DNA.

4.1. Construction of Vector Containing Interferon Analogs, HSA/INF-α-1b

Interferon-a-1b was fused to HAS C'-terminus by using the following PCR primers:
SEQ ID NO. 37: 5'-CTGCCTTAGGCTTA TGTGATCTCCCTGAGACCC-3' and SEQ ID NO. 38: 5'-T CTCGAGTTACTTCCTCCTTAATCTTTC-3'. (Human interferon-a-1b mature protein sequence is underlined in SEQ ID NO. 37).

A Xho I site (underlined in SEQ ID NO. 38) was created at the 3' end of interferon-α-1b gene. The PCR products were digested with Bsu36I and Xho I, and the fragment was gel purified and inserted into pYZ-HSA or pYH-HSA between of Bsu36 I and Xho I sites to generate a new plasmid DNA, pYZ-HSA/IFN-α. The HSA-hIFN-α-1b hybrid polynucleotide sequence (SEQ ID NO. 1) and its fusion protein amino acid sequence (SEQ ID NO. 2) are showed in FIG. 1.

4.2. Construction of Vector Containing Interferon Analogs, HSA/INF-α-2a and HSA/IFN-α-2b Interferon-α-2a or Interferon-α-2b gene was fused to HSA C'-terminus by using the following PCR primers:
SEQ ID NO. 39: 5'-CTGCCTTAGGCTTA TGTGATCTGCCTCAAACCC-3'. (Human Interferon-α-2a and Interferon-α-2b mature protein sequence is underlined), and

SEQ ID NO. 40: 5'-T CTCGAGTCATTCCTTACTTCTTAAAC-3'.

A Xho I site (underlined in SEQ ID NO. 40) was created at the 3' end of interferon-α gene. The PCR products were digested with Bsu36I and Xho I, and the fragment was gel purified and inserted into pYZ-HSA or pYH-HSA between of Bsu36 I and Xho I sites to generate a new plasmid DNA, pYZ-HSA/IFN-α. The HSA-hIFN-α-2b hybrid polynucleotide sequence (SEQ ID NO. 3) and its fusion protein amino acid sequence (SEQ ID NO. 4) are showed in FIG. 1.

4.3. Construction of Vector Containing Analog of Interferon-β, HSA/IFN-β

To make an analog of Interferon-β, HSA-IFN-β fusion protein, the following primers were designed SEQ ID NO. 41:

5'-CTGCCTTAGGCTTATACAACTTGCTTGGATTCC-3' (human interferon-β mature protein sequence underlined), and SEQ ID NO. 42:

5'-CACTCGAGTCAGTTTCGGAGGTAACC-3'

(Xho I site underlined) and used to generate the modified human interferon-β DNA fragment. The PCR products were inserted between Bsu36I and Xho I sites of pYZ-HSA or pYH-HSA to generate a pYZ-HSA/IFN-β or pYH-HSA/IFN-β. The HSA-IFN-β hybrid polynucleotide sequence (SEQ ID NO. 5) and its fusion protein amino acid sequence (SEQ ID NO. 6) are shown in FIG. 1.

4.4. Construction of Vector Containing analog of Interferon-ω, HSA/IFN-ω

Human interferon-ω gene was fused with HSA DNA sequence by using two primers:

SEQ ID NO. 43: 5'-CTGCCTTAGGCTTA TGTGATCTGCCTCAGAACCATGG-3' (Interferon-ω mature protein sequence underlined), and SEQ ID NO. 44: 5'-CTCGAGTCAAGATGAGCCCAGGTCTC-3' (Xho I site at the 3'-terminus of interferon-o) underlined).

The PCR products were gel purified and subcloned between Bsu36I and Xho I sites of pYZ-HAS or pYH-HSA to generate a pYZ-HSA/IFN-w or pYH-HSA/IFN-ω. The analog of interferon-ω, HSA-INF-ω hybrid polynucleotide, sequence (SEQ ID NO. 7) and its amino acid sequence (SEQ ID NO. 8) are shown in FIG. 1.

4.5. Construction of Vector Containing Analog of Interferon-γ, HSA/IFN-γ

The following primers:
SEQ ID NO. 45: 5'-ACTCCTTAGGCTTA CAGGACCCATATGTACAAGAAGC-3' (Interferon-γ mature protein sequence underlined), and

SEQ ID NO. 46: 5'-CTCGAGTTACTGGGATGCTCTTCG-3'

(Xho I site underlined) were used to modify Interferon-γ DNA sequence in order to subclone it into pYZ-HSA vector. PCR products were gel purified and double digested with Bsu36 I and Xho I and inserted between Bsu36 I and XhoI sites of pYZ-HSA, pYH-HSA to generate a pYZ-HSA/IFN-g, pYH-HSA/IFN-γ. The analog of Interferon-γ, HSA/IFN-γ hybrid polynucleotide, sequence (SEQ ID NO. 9) and its fusion protein amino acid sequence (SEQ ID NO. 10) are shown in FIG. 1.

5. Transformation of Yeast

An expression cassette contains, a promoter driving of a gene, here is the analog of Interferon, a terminator, and a selective marker (such as Zeocin, antibiotic selection; Histidine, a deficient selection). Yeast strains, GS115, SMD1168 or ZY101 are Histidine synthesis deficiency. When transform the Yeast with the linearized yeast transfer shuttle vector, the expression cassette will be inserted directly to the location with a homologue region recombination. Most time one cassette will be inserted into a yeast host. In here, we disclosed a novel method for making of a dual insertion of expression cassette into a different chromosome region by two vectors with two different select markers.

5.1. Single Expression Cassette Insertion on Yeast

A yeast *Pichia pastoris* strain, GS 115, colony was inoculated into 5 ml of YPD medium in a 50 ml conical tube at 30° C. overnight with shaking at 250 rpm. 0.2 ml of the culture was inoculated into 500 ml of YPD medium continually shaking at 30° C. for further 2-3 hours or until the cell density reach to $OD_{600}$=1.3-1.5. The cells were collected by centrifugation. The cell pellets were resuspend in 500 ml of ice-cold sterile water in order to wash the cells. After two rounds of washing, the cells were resuspended in 20 ml of ice-cold 1 M sorbitol to wash again and finally suspended in 1 ml of ice-cold 1M sorbitol. The plasmid DNA constructs from Example 2, pYZ-HSA and in Example 4, pYZ-HSA/IFN-α-2a, pYZ-HSA/IFN-α-2b, pYZ-HSA/IFN-β, and pYZ-HSA/IFN-ω, pYZ-HSA/IFN-γ were linearized by PmeI restriction enzyme digestion first.

5 μg of each linear plasmid DNA was used to transform 80 μl of the freshly made yeast cells in an ice-cold 0.2 cm electroporation cuvette. The cells mixed with plasmid DNA were pulsed for 5-10 ms with field strength of 7500 V/cm. After the pulse, 1 ml of ice-cold 1M sorbitol was immediately added into the cuvette and the content was transferred to a sterile 15 ml tube. The transformed cells were incubated in 30° C. without shaking for 2 hours then spread on pre-made YPD-agar plates with 100 μg/ml Zeocin. The colonies were identified with the insert and the expression level by SDS-PAGE or western-blot with proper antibodies. Different strains of *Pichia*, such as X-33, KM71 and proteinase deficient strain SMD1168, ZY101 (Constructed and be used in manufacture of recombinant secretory protein drugs by yeast system, Zailin YU unpublished data 2002) were tested for the expression and secretory of recombinant proteins.

5.2. Dual Expression Cassette Insertion on Yeast

In order to gain a higher expression level, people are trying to select multi-insertion from the recombinant yeast (Invitrogen Corp), But the select is no efficient, we use a second transformation method on a yeast is carrying an expression cassette. To do this, for example, we use pYZ-HSA/IFN-β transformed yeast, the HSA/IFN-β expression cassette has inserted at AOX1 Gene location in yeast chromosome with a Zeocin resistance, transformed again with pYH-HSA/IFN-β expression cassette by the method described in section of 5.1 again. The new select marker will be on the YPD-Agar plate contains no Histidine (His⁻). Only the recombinant yeast contains the expression cassette with a Histidine gene can be survived in the medium. The new recombinant yeast now contains two genes of HSA/IFN-β, one located on AOX1 gene location, one is located on Histidinol dehydrogenase location. This recombinant yeast contains two selective markers and can grow in conditioned medium with antibiotic Zeocin, without the amino acid, Histidine, supplement.

By using this method, a different expression cassette also can be inserted to the yeast chromosome, such as the first expression cassette contains an interferon-a, and the second one is an interferon-γ; or the first expression cassette contains protein-X and the second expression cassette contains protein-X or protein different than first protein-X.

6. Secretion and Characterization of Interferon Analogs Expressed by *Pichia*

Several colonies from each transformation of the Interferon analog, HSA-IFN, were cultured with Zeocin in the buffered minimal medium with glycerol overnight or until $OD_{600}$=2-6 at 30° C. and shaking at 300 rpm. The cultured cells were collected by centrifuge at 1500 rpm for 5 minutes. Resuspend the cells into buffered minimal medium without glycerol and cell densities was keep in $OD_{600}$=1.0. 100% methanol was added into each flask to a final concentration at 0.5% every 24 hours to induce the protein expression. The culture medium was collected at different time points and the expression of each fusion protein was confirmed by SDS-PAGE and western blot. The results showed that human albumin and HSA-IFN fusion protein were expressed and secreted into the medium.

Figure 3:
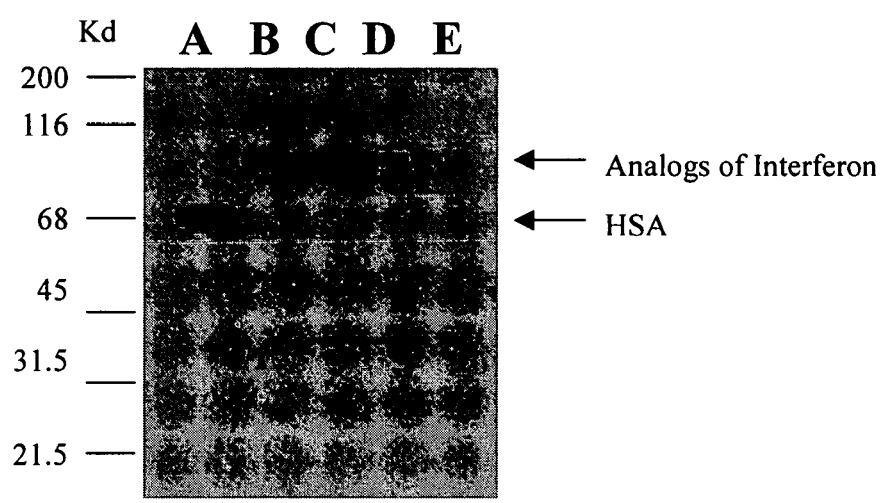
FIG. 3 shows a Western blot detected using mouse monoclonal anti-human serum albumin (Sigma Cat# A6684). Each lane was load with equivalent of 10 μl of culture medium supernatant from yeast after three-day expression. A), HSA (65 Kd); B), Analog IFN-α-2a (84 Kd); C). Analog IFN-β (84 kd); D). Analog IFN-ω (84 kd); E). Control (yeast parent strain culture).
Figure 4:
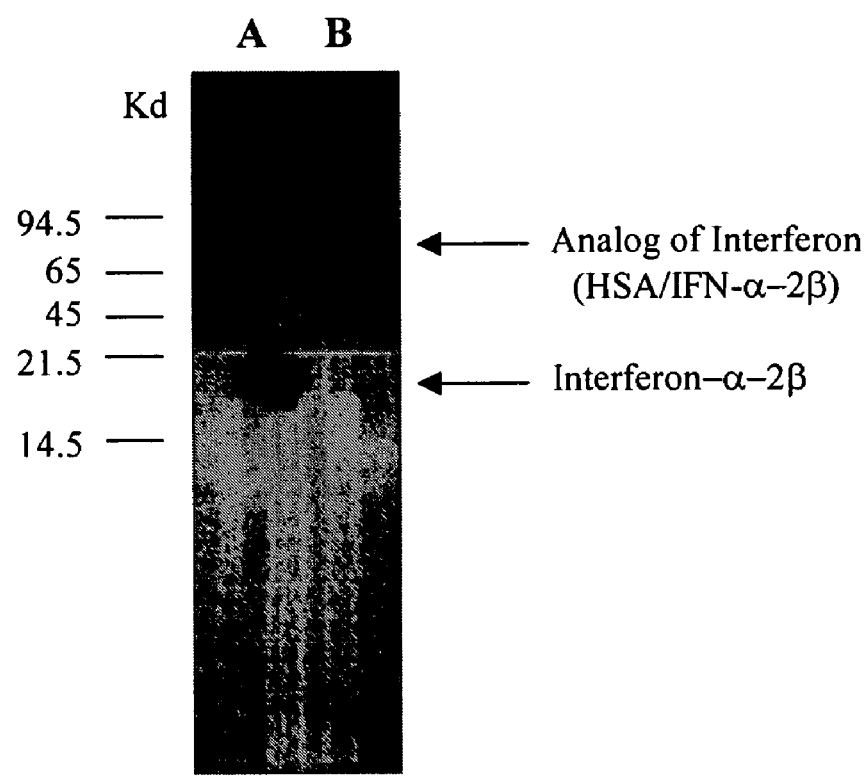
FIG. 4 shows a Western blot detected using Rabbit polyclonal anti-hIFN-α-2a antibody (Chemicon International Inc., Cat# Ab-218-NA), each lane contains 100 ng proteins. A), human IFN-α-2b (19 kd) expressed by $E.\ coli$; B), Analog Interferon-α 84 kd, HSA/IFN-α-2b fusion protein, expressed by yeast.

Mouse monoclonal anti-human serum albumin (Sigma) was used for immunoblotting on a SOS-PAGE gel. A typical Western blot experiment was carried on by electrophoresis transfer the protein from SOS-PAG to a nylon or nitrocellulose filter and incubated with a specific antibody (as the "first antibody"). Then an anti-first antibody would add to binding on the first antibody (as the "second antibody"). The second antibody was labeled with Fluorescence and the filter was exposed to an X-ray film. Protein molecular weight standard was used to determine the protein size. The results (FIG. 3) showed that the expressed recombinant proteins, HSA, Analog of Interferon-α (HSA-IFN-α-2a) therapeutic fusion protein, had an expected molecular weight and also had the same antigen as that of HSA prepared from a human blood plasma (Sigma). Using monoclonal anti-IFN-α specific antibody as first antibody, the HSA/Interferon-α fusion protein and human interferon-α (Chemicon International Inc. US) had the same antigen and showed that the molar ratio of HSA to interferon-α in the HAS/IFN-α-2a fusion protein is as expected (see Zailin YU Provisional Patent ADDlication Ser. No. 60/392,948). Using monoclonal anti-Interferon-α specific antibody (CII, US) as first antibody, the HSA-IFN-α fusion protein and human Interferon-α (CII, US) had the same antigen and showed that the molar ratio of HSA to lnterferon-β in the HSA/IFN-α fusion protein is as expected (FIG. 4).

7. Purification and Molecular Characterization of Interferon Analogs, HSA-IFNs The cell culture medium (supernatant) containing the secreted protein of HSA or HSA-IFN fusion protein produced from the recombinant *Pichia* was collected, the salt concentration reduced, and the pH was adjusted to above 7.5. The concentrated sample was passed through an Affi-Gel Blue-gel (50-100 mesh) (Bio-Rad). The albumin or albumin fusion protein was bound to the matrix and eluded by a gradient 1-5M NaCl. 75-85% pure albumin or albumin-IFN can be recovered in this step. If further purification is necessary, a size exclusion chromatography is applied to give a 95-99% purity of proteins. The pyrogen was removed from the protein samples in order to meet the requirement for use in in vivo test. The Affi-Prep Polymyxin Support (BIO-Rad) column was used to remove endotoxin from the samples. The purified protein finally passed through 0.2 μM filter to be sterilized and the protein concentration was measured by a standard method by using a Bio-Rad Protein Assay Kit.

8. Viral Protection Assay of Interferon Analog, Human Interferon-α-2a

Figure 5:
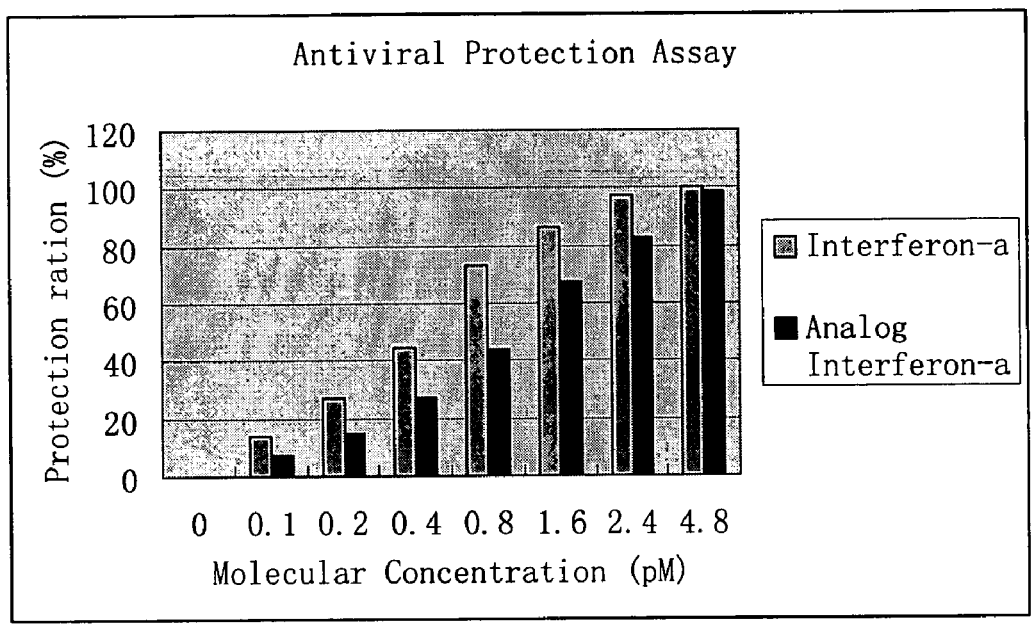
FIG. 5 is an Antiviral infection assay for human IFN-α and Analog Interferon-α, HSA/IFN-α-2a fusion protein, in WISH cell with VSV challenges.

Antiviral activity of IFN-α-2a and its derivatives was determined by the capacity of the cytokine to protect human amnion WISH cells against vesicular stomatitis virus (VSV)-induced cytopathic effects (Rubinstein, et al., 1981, *J. Virol.* 37, 755-758). WISH cells ($4.5 \times 10^5$ cells/ml) were seeded in a 96-well plate (100 μl/well) and incubated with 2-fold serial dilutions of IFN-α-2a or interferon analog, HSA/IFN-α-2a for 18 h at 37° C. WISH cell viability was determined by measuring the absorbance of crystal violet-stained cells in an ELISA plate. In this assay, native IFN-α-2a shows 50% protection of VSV-induced WISH cells ($ED_{50}$) at a concentration of 0.45±0.04 pM. The IFN-α-2a analog exhibiting $ED_{50}$ of 1.13±0.3 pM in this assay was considered as having 25% of the native antiviral potency (FIG. 5). Since HSA (65 kd) has a molecular weight about 3 times higher than that of interferon (19 kd), it can be inferred that HSA-IFN-α-2a fusion protein and Interferon analog have the same bioactivity as that of human Interferon-α-2a alone based on the molecular ratio.

9. Bioassay of Interferon-α Analog, HSA/IFN-α, by ELISA

Enzyme-linked immunosorbent assay (ELISA) kit from Chemicon International, Inc. (California, US) was used for the quantitative determination of Interferon-concentration and bioactivities comparison with a commercial IFN-α sample. The IFN-α ELISA is based on the double-antibody sandwich method. With the ChemiKine™ assay system, pre-coated goat anti-rabbit antibody plates are used to capture a specific IFN-α complex in each sample consisting of IFN-α antibody, biotinylated IFNα, and sample/standard. The biotinylated IFNα conjugate (competitive ligand), and sample or standard compete for IFNα specific antibody binding sites. Therefore, as the concentration of IFN-α in the sample increases, the amount of biotinylated IFNα captured by the antibody decreases. The assay is visualized using a streptavidin alkaline phosphatase conjugate and an ensuing chromagenic substrate reaction. The amount of IFNα detected in each sample is compared to an IFN-α standard curve which demonstrates an inverse relationship between Optical Density (O.D.) and cytokine concentration: i.e. the higher the O.D. the lower the cytokine concentration in the sample. The amount of color generated was directly proportional to the amount of conjugate bound to the IFN-α antibody complex, which, in turn, was directly proportional to the amount of IFN-α in the protein samples or standard. The absorbance of this complex was measured and a standard curve was generated by plotting absorbance versus the concentration of the IFN-α standards. The IFN-α concentration of the unknown sample was determined by comparing the optical density of the protein samples to the standard curve. The standards used in this assay were recombinant human IFN-α (with kit) calibrated against the Second International Reference Preparation (67/343), a urine-derived form of human IFN-α. Human recombinant IFN-α expressed in CHO cells was used as a control to determine the rHSA/IFN-α bio-activity.

The results showed that the bioactivity of IFN-α fused to HSA had same activity compared with the native Interferon-α. When in a higher concentration of HSA-IFN-α in a sample, the size of HSA-IFN-α fusion protein molecule may be too large, which prevents the anti-IFN-α antibody from efficiently binding to the IFN-α molecule fused to HSA, thereby the sensitivity of the detection in this bioassay would be reduced. Same results were observed in HSA-EPO ELISA experiments (YU and FU, US20040063635).

10. Stability Testing of Interferon Analogs, HSA-IFNs Fusion Proteins In Vitro Using HSA/IFN-α-2a as an example, the stability of this interferon analog, HSA-interferons fusion protein, was tested at different time points at 37° C. and 50° C. 50 U (0.5 ng) of human interferon-α-2a from bacteria or 50 U (19.6 ng) of rHSA/IFN-α-2a was put into 200 μl thin-well PCR tube with 200 μl of tissue culture medium RPM1 without fetal bovine serum and other components. The tubes were sealed and left in water both. Samples were taken out at different time points and immediately put into −80° C. for storage. After all of samples were collected, a viral infection test on Wish cell line was carried out by standard protocols. The control of the test was set up in the same way as that in the bioassay. The results were showed that the "naked" human IFN-α lost almost all of its bioactivity after 10 hours at 37° C. (in FIG. 6 Panel A). But after 24 hours in 37° C., the bioactivity of Interferon Analog, HSA/IFN-α, still remained no changes. Experiment shows that even after 10 days, the antivirus potency has at least half remained. At 50° C. (Panel B), the "naked" human IFN-α lost its the bioactivity completely in 1 days. The Interferon Analog, HSA/IFN-α fusion protein, still retained near 90% of its bioactivity after 5 days. These results indicate that interferon analog may have a longer storage time and more resistant to degradation in harsh environment such as high temperatures.

11. Long Acting of Interferon Analogs in Plasma

Human Interferon Analogs, human serum albumin-interferon-α-2b (HSA/IFN-α-2b) and Interferon-α-2b, were tested for the long acting bio-function or slow release in animal in vivo. 15 ng (about $1 \times 10^3$ U) human Interferon-α-2b plus 45 ng HSA (recombinant HAS from yeast) or 60 ng (about $1 \times 10^3$ U) human interferon-α-2b analog was injected into rats with 100 µl solution. After injection, the blood samples (0.05 ml) were collected. In the last day of experiments, a 05 ml of blood was collected from all the tested rats. The blood sample with EDTA added was spun in a microcentrafuge tube. Blood supernatant was collected and stored at −80° C. Using Chemicon International, Inc. (California, USA) ChemiKine™ Human IFN-α EIA Kit (Cat# CYT102) all blood samples from the rats injected with interferon-α-2b (control) and Interferon Analog, HSA/IFN-α-2b were tested. The results showed that Interferon analog maintained much longer undigested status in plasma than the "naked" interferon-α-2b even with same amount of HSA injection (FIG. 7). The interferon-α-2 could only be detected from plasma in about 10 hours. The Interferon analog, HSA/IFN-α-2b could be detected even after 12 days of injection. This result is also consistent with the report that albumin has a half-life in plasma about 20 days (Waldmann T. A., in "Albumin Structure, Function and Uses", Rosenoer V. M. et al (eds), Pergamon Press, Oxford, 255-275, 1977). The instant novel form interferon analog shows a greater half-life in plasma. The plasma samples at day 12 were tested for their antiviral protection to WISH cells. The results showed that the control sample has no antiviral protection bio-function, but the instant Interferon analog still maintains some bio-function in viral protection to the tested cells. This long acting bio-function gives Interferon analogs novel utilities as a recombinant protein drugs for therapeutic treatment of patients.

12. Expression and Scale-Up of Interferon Analogs by Fermentation

In this example, it is shown that expression and scale-up are much easier by using a *Pichia* system than other currently available systems. After *Pichia* recombinants were isolated, expression of both Mut+ and Mut$^s$ recombinants was tested. This involved growing a small culture of each recombinant, inducing with methanol, and taking sample at different time points. For secrete expression, both the cell pellet and supernatant were analyzed from each time point. The samples were analyzed on SDS-PAGE gels by using both Coomassie staining and Western blot. Bioactivities of expressed samples were tested and the expression levels and purity were monitored in each step for production of HSA fusion proteins.

REFERENCES

Brown, J. R. "Albumin structure, Function, and Uses" Pergamon, New York, 1977
Weikamp L, R, et al., Ann. Hum. Genet., 37 219-226, 1973
Carter D. C. et al., Science 244, 1195-1198, 1989
Waldmann T. A., in "Albumin Structure, Function and Uses", Rosenoer V. M. et al (eds), Pergamon Press, Oxford, 255-275, 1977
Shechter et al., Proc. Natl. Acad. Sci. USA. 2001 Jan. 30; 98 (3): 1212-1217
O'Kelly, et al., 1985. *Proc. Soc. Exp. Biol. Med.* 178, 407-411
Rostaing, et al., 1998, *J. Am. Soc. Nephrol.* 9, 2344-2348
Vilcek (1991) "Interferons", in "Peptide Growth Factors and Their Receptors II", edited by Sporn and Roberts, Spring-Verlag Heidelberg, New York Inc., USA. pp 3-38

PATENT REFERENCES

EP 330 451
EP 361 991
U.S. Pat. No. 5,098,703
U.S. Pat. No. 4,973,479.
U.S. Pat. No. 4,975,276
U.S. Pat. No. 5,082,658
U.S. Pat. No. 6,174,996
U.S. Pat. No. 5,908,621
U.S. Pat. No. 4,892,743
U.S. Pat. No. 5,723,125
U.S. Pat. No. 5,324,655
U.S. Pat. No. 5,190,751

What is claimed is:

1. A recombinant protein comprising (a) the amino acid sequence of SEQ ID NO: 4; or (b) the amino acid sequence encoded by the polynucleotide of SEQ ID NO: 3.

2. The recombinant protein of claim 1, wherein said protein is a fusion protein of human serum albumin (HSA) and human interferon-α-2b (IFN-α-2b).

3. The recombinant protein of claim 2, wherein said fusion protein has a plasma half-life that is 3 times longer than that of IFN-α-2b alone when administered in vivo.

4. The recombinant protein of claim 3, wherein said fusion protein has a shelf life that is 5 times longer than that of IFN-α-2b alone when stored under a same condition.

5. The recombinant protein of claim 4, wherein said recombinant protein binds to an antibody of human albumin.

6. The recombinant protein of claim 1, wherein said protein is recombinantly produced in a host cell selected from the group consisting of mammalian cells and yeast cells.

7. The recombinant protein of claim 6, wherein said yeast cells are selected from the group consisting of *Saccharomyces, Hansenula, Candida, Pichia, Kluyveromyces, Torulaspora* and *Schinosaccharomyces*.

8. The recombinant protein of claim 7, wherein said *Pichia* yeast cells are *Pichia pastoris* cells.

9. The recombinant protein of claim 6, wherein said host cell contains a recombinant vector comprising the polynucleotide of SEQ ID NO: 3.

10. A composition comprising the recombinant protein of claim 1.

11. The composition of claim 10 further comprising a second human serum albumin-interferon fusion protein.

12. The composition of claim 11, wherein said second human serum albumin-interferon fusion protein comprises human serum albumin-interferon-β fusion protein, human serum albumin-interferon-γ fusion protein, or human serum albumin-interferon-ω fusion protein.

13. A kit comprising the recombinant protein of claim 1 and a second human serum albumin-interferon fusion protein.

14. The kit of claim 13, wherein said second human serum albumin-interferon fusion protein comprises human serum albumin-interferon-β fusion protein, human serum albumin-interferon-γ fusion protein, or human serum albumin-interferon-ω fusion protein.

* * * * *

SEQUENCE LISTING

```
<160> NUMBER OF SEQ ID NOS: 46

<210> SEQ ID NO 1
<211> LENGTH: 2325
<212> TYPE: DNA
<213> ORGANISM: Artificial Sequence
<220> FEATURE:
<223> OTHER INFORMATION: Synthesis

<400> SEQUENCE: 1
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca aagccttggt gttgattgcc tttgctcagt atcttcagca gtgtccattt     180
gaagatcatg taaaattagt gaatgaagta actgaatttg caaaaacatg tgttgctgat     240
gagtcagctg aaaattgtga caaatcactt catacccttt tggagacaa attatgcaca      300 gttgcaactc ttcgtgaaac ctatggtgaa atggctgact gctgtgcaaa acaagaacct     360
gagagaaatg aatgcttctt gcaacacaaa gatgacaacc caaacctccc ccgattggtg     420
agaccagagg ttgatgtgat gtgcactgct tttcatgaca atgaagagac attttttgaaa    480 aaatacttat atgaaattgc cagaagacat ccttactttt atgccccgga actccttttc     540
```

-continued

```
tttgctaaaa ggtataaagc tgcttttaca gaatgttgcc aagctgctga taaagctgcc     600
tgcctgttgc caaagctcga tgaacttcgg gatgaaggga aggcttcgtc tgccaaacag     660
agactcaagt gtgccagtct ccaaaaattt ggagaaagag ctttcaaagc atgggcagta     720
gctcgcctga gccagagatt tcccaaagct gagtttgcag aagtttccaa gttagtgaca     780
gatcttacca agtccacac ggaatgctgc catgagatc tgcttgaatg tgctgatgac      840
agggcggacc ttgccaagta tatctgtgaa atcaagatt cgatctccag taaactgaag      900
gaatgctgtg aaaaacctct gttggaaaaa tcccactgca ttgccgaagt ggaaaatgat     960
gagatgcctg ctgacttgcc ttcattagct gctgattttg ttgaaagtaa ggatgtttgc    1020
aaaaactatg ctgaggcaaa ggatgtcttc ctgggcatgt ttttgtatga atatgcaaga    1080
aggcatcctg attactctgt cgtgctgctg ctgagacttg ccaagacata tgaaaccact    1140
ctagagaagt gctgtgccgc tgcagatcct catgaatgct atgccaaagt gttcgatgaa    1200
tttaaacctc ttgtggaaga gcctcagaat ttaatcaaac aaaattgtga gcttttgag     1260
cagcttggag agtacaaatt ccagaatgcg ctattagttc gttacaccaa gaaagtaccc    1320
caagtgtcaa ctccaactct tgtagaggtc tcaagaaacc taggaaaagt gggcagcaaa    1380
tgttgtaaac atcctgaagc aaaaagaatg ccctgtgcag aagactatct atccgtggtc    1440
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaagagca actgaaagct gttatggatg atttcgcagc ttttgtagag     1740
aagtgctgca aggctgacga taaggagacc tgctttgccg aggagggtaa aaaacttgtt    1800
gctgcaagtc aagctgcctt aggcttatgt gatctccctg agacccacag cctggataac    1860
aggaggacct tgatgctcct ggcacaaatg agcagaatct ctccttcctc ctgtctgatg    1920
gacagacatg actttggatt tccccaggag gagtttgatg caaccagtt ccagaaggct     1980
ccagccatct ctgtcctcca tgagctgatc cagcagatct tcaacctctt taccacaaaa    2040
gattcatctg ctgcttggga tgaggacctc ctagacaaat tctgcaccga actctaccag    2100
cagctgaatg acttggaagc ctgtgtgatg caggaggaga gggtgggaga aactccctg     2160
atgaatgcgg actccatctt ggctgtgaag aaatacttcc gaagaatcac tctctatctg    2220
acagagaaga aatacagccc ttgtgcctgg gaggttgtca gagcagaaat catgagatcc    2280
ctctctttat caacaaactt gcaagaaaga ttaaggagga agtaa                    2325
```

```
<210> SEQ ID NO 2
<211> LENGTH: 750
<212> TYPE: PRT
<213> ORGANISM: Artificial Sequence
<220> FEATURE:
<223> OTHER INFORMATION: Synthesis

<400> SEQUENCE: 2

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
35                  40                  45
```

```
Phe Ala Lys Thr Cys Val Ala Asp Glu Ser Ala Glu Asn Cys Asp Lys
 50              55                  60

Ser Leu His Thr Leu Phe Gly Asp Lys Leu Cys Thr Val Ala Thr Leu
 65              70                  75                      80

Arg Glu Thr Tyr Gly Glu Met Ala Asp Cys Cys Ala Lys Gln Glu Pro
             85                  90              95

Glu Arg Asn Glu Cys Phe Leu Gln His Lys Asp Asp Asn Pro Asn Leu
        100             105             110

Pro Arg Leu Val Arg Pro Glu Val Asp Val Met Cys Thr Ala Phe His
115             120             125

Asp Asn Glu Glu Thr Phe Leu Lys Lys Tyr Leu Tyr Glu Ile Ala Arg
130             135             140

Arg His Pro Tyr Phe Tyr Ala Pro Glu Leu Leu Phe Phe Ala Lys Arg
145             150             155             160

Tyr Lys Ala Ala Phe Thr Glu Cys Cys Gln Ala Ala Asp Lys Ala Ala
            165             170             175

Cys Leu Leu Pro Lys Leu Asp Glu Leu Arg Asp Glu Gly Lys Ala Ser
180             185             190

Ser Ala Lys Gln Arg Leu Lys Cys Ala Ser Leu Gln Lys Phe Gly Glu
195             200             205

Arg Ala Phe Lys Ala Trp Ala Val Ala Arg Leu Ser Gln Arg Phe Pro
210             215             220

Lys Ala Glu Phe Ala Glu Val Ser Lys Leu Val Thr Asp Leu Thr Lys
225             230             235             240

Val His Thr Glu Cys Cys His Gly Asp Leu Leu Glu Cys Ala Asp Asp
            245             250             255

Arg Ala Asp Leu Ala Lys Tyr Ile Cys Glu Asn Gln Asp Ser Ile Ser
        260             265             270

Ser Lys Leu Lys Glu Cys Cys Glu Lys Pro Leu Leu Glu Lys Ser His
275             280             285

Cys Ile Ala Glu Val Glu Asn Asp Glu Met Pro Ala Asp Leu Pro Ser
290             295             300

Leu Ala Ala Asp Phe Val Glu Ser Lys Asp Val Cys Lys Asn Tyr Ala
305             310             315             320

Glu Ala Lys Asp Val Phe Leu Gly Met Phe Leu Tyr Glu Tyr Ala Arg
            325             330             335

Arg His Pro Asp Tyr Ser Val Val Leu Leu Leu Arg Leu Ala Lys Thr
        340             345             350

Tyr Glu Thr Thr Leu Glu Lys Cys Cys Ala Ala Ala Asp Pro His Glu
355             360             365

Cys Tyr Ala Lys Val Phe Asp Glu Phe Lys Pro Leu Val Glu Glu Pro
370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
            405             410             415

Glu Val Ser Thr Pro Thr Leu Val Glu Val Ser Arg Asn Leu Gly Lys
        420             425             430

Val Gly Ser Lys Cys Cys Lys His Pro Glu Ala Lys Arg Met Pro Cys
435             440             445

Ala Glu Asp Tyr Leu Ser Val Val Leu Asn Gln Leu Cys Val Leu His
450             455             460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Cys Asp Leu Pro Glu Thr His
        580                 585                 590

Ser Leu Asp Asn Arg Arg Thr Leu Met Leu Leu Ala Gln Met Ser Arg
595                 600                 605

Ile Ser Pro Ser Ser Cys Leu Met Asp Arg His Asp Phe Gly Phe Pro
610                 615                 620

Gln Glu Glu Phe Asp Gly Asn Gln Phe Gln Lys Ala Pro Ala Ile Ser
625                 630                 635                 640

Val Leu His Glu Leu Ile Gln Gln Ile Phe Asn Leu Phe Thr Thr Lys
            645                 650                 655

Asp Ser Ser Ala Ala Trp Asp Glu Asp Leu Leu Asp Lys Phe Cys Thr
        660                 665                 670

Glu Leu Tyr Gln Gln Leu Asn Asp Leu Glu Ala Cys Val Met Gln Glu
675                 680                 685

Glu Arg Val Gly Glu Thr Pro Leu Met Asn Ala Asp Ser Ile Leu Ala
690                 695                 700

Val Lys Lys Tyr Phe Arg Arg Ile Thr Leu Tyr Leu Thr Glu Lys Lys
705                 710                 715                 720

Tyr Ser Pro Cys Ala Trp Glu Val Val Arg Ala Glu Ile Met Arg Ser
            725                 730                 735

Leu Ser Leu Ser Thr Asn Leu Gln Glu Arg Leu Arg Arg Lys
        740                 745                 750

<210> SEQ ID NO 3
<211> LENGTH: 2325
<212> TYPE: DNA
<213> ORGANISM: Artificial Sequence
<220> FEATURE:
<223> OTHER INFORMATION: Synthess

<400> SEQUENCE: 3
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca agccttggt gttgattgcc tttgctcagt atcttcagca gtgtccattt     180
gaagatcatg taaaattagt gaatgaagta actgaatttg caaaaacatg tgttgctgat     240
gagtcagctg aaaattgtga caaatcactt catacccttt ttggagacaa attatgcaca     300
gttgcaactc ttcgtgaaac ctatggtgaa atggctgact gctgtgcaaa acaagaacct     360
gagagaaatg aatgcttctt gcaacacaaa gatgacaacc caaacctccc ccgattggtg     420
agaccagagg ttgatgtgat gtgcactgct tttcatgaca atgaagagac attttgaaa     480
```

```
aaatacttat atgaaattgc cagaagacat ccttactttt atgccccgga actccttttc      540
tttgctaaaa ggtataaagc tgcttttaca gaatgttgcc aagctgctga taaagctgcc      600
tgcctgttgc caaagctcga tgaacttcgg atgaaggga aggcttcgtc tgccaaacag       660
agactcaagt gtgccagtct ccaaaaattt ggagaaagag ctttcaaagc atgggcagta      720
gctcgcctga ccagagatt tcccaaagct gagtttgcag aagtttccaa gttagtgaca       780
gatcttacca aagtccacac ggaatgctgc catggagatc tgcttgaatg tgctgatgac      840
agggcggacc ttgccaagta tatctgtgaa atcaagatt cgatctccag taaactgaag       900
gaatgctgtg aaaaacctct gttggaaaaa tcccactgca ttgccgaagt ggaaaatgat      960
gagatgcctg ctgacttgcc ttcattagct gctgattttg ttgaaagtaa ggatgtttgc     1020
aaaaactatg ctgaggcaaa ggatgtcttc ctgggcatgt ttttgtatga atatgcaaga     1080
aggcatcctg attactctgt cgtgctgctg ctgagacttg ccaagacata tgaaaccact     1140
ctagagaagt gctgtgccgc tgcagatcct catgaatgct atgccaaagt gttcgatgaa     1200
tttaaacctc ttgtggaaga gcctcagaat ttaatcaaac aaaattgtga gcttttgag      1260 cagcttggag agtacaaatt ccagaatgcg ctattagttc gttacaccaa gaaagtaccc     1320
caagtgtcaa ctccaactct tgtagaggtc tcaagaaacc taggaaaagt gggcagcaaa     1380
tgttgtaaac atcctgaagc aaaaagaatg ccctgtgcag aagactatct atccgtggtc     1440
ctgaaccagt tatgtgtgtt gcatgagaaa acgccagtaa gtgacagagt caccaaatgc     1500
tgcacagaat ccttggtgaa caggcgacca tgcttttcag ctctggaagt cgatgaaaca     1560
tacgttccca aagagtttaa tgctgaaaca ttcaccttcc atgcagatat atgcacactt     1620
tctgagaagg agagacaaat caagaaacaa actgcacttg ttgagcttgt gaaacacaag     1680
cccaaggcaa caaagagca actgaaagct gttatggatg atttcgcagc ttttgtagag      1740
aagtgctgca aggctgacga taaggagacc tgctttgccg aggagggtaa aaaacttgtt     1800
gctgcaagtc aagctgcctt aggcttatgt gatctgcctc aaacccacag cctgggtagc     1860
aggaggacct tgatgctcct ggcacagatg aggaaaatct ctcttttctc ctgcttgaag     1920
gacagacatg actttggatt tccccaggag gagtttggca accagttcca aaaggctgaa     1980
accatccctg tcctccatga gatgatccag cagatcttca atctcttcag cacaaaggac     2040
tcatctgctg cttgggatga acctcctca gacaaattct acactgaact ctaccagcag     2100
ctgaatgacc tggaagcctg tgtgatacag ggggtgggg tgacagagac tcccctgatg     2160
aaggaggact ccattctggc tgtgaggaaa tacttccaaa gaatcactct ctatctgaaa     2220
gagaagaaat acagcccttg tgcctgggag gttgtcagag cagaaatcat gagatctttt     2280
tctttgtcaa caaacttgca agaaagttta agaagtaagg aatga                    2325
```

<210> SEQ ID NO 4
<211> LENGTH: 750
<212> TYPE: PRT
<213> ORGANISM: Artificial Sequence
<220> FEATURE:
<223> OTHER INFORMATION: Synthesis

<400> SEQUENCE: 4

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30
```

```
Gln Cys Pro Phe Glu Asp His Val Lys Leu Val Asn Glu Val Thr Glu
 35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
            165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
            245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
            325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
            405                 410                 415
Glu Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
435                 440                 445
Ala Glu Asp Tyr Leu Ser Val Val Leu Asn Gln Leu Cys Val Leu His
```

-continued

```
              450               455               460
Glu Lys Thr Pro Val Ser Asp Arg Val Thr Lys Cys Cys Thr Glu Ser
465               470               475               480

Leu Val Asn Arg Arg Pro Cys Phe Ser Ala Leu Glu Val Asp Glu Thr
            485               490               495

Tyr Val Pro Lys Glu Phe Asn Ala Glu Thr Phe Thr Phe His Ala Asp
        500               505               510

Ile Cys Thr Leu Ser Glu Lys Glu Arg Gln Ile Lys Lys Gln Thr Ala
515               520               525

Leu Val Glu Leu Val Lys His Lys Pro Lys Ala Thr Lys Glu Gln Leu
530               535               540

Lys Ala Val Met Asp Asp Phe Ala Ala Phe Val Glu Lys Cys Cys Lys
545               550               555               560

Ala Asp Asp Lys Glu Thr Cys Phe Ala Glu Glu Gly Lys Lys Leu Val
            565               570               575

Ala Ala Ser Gln Ala Ala Leu Gly Leu Cys Asp Leu Pro Gln Thr His
            580               585               590

Ser Leu Gly Ser Arg Arg Thr Leu Met Leu Leu Ala Gln Met Arg Lys
595               600               605

Ile Ser Leu Phe Ser Cys Leu Lys Asp Arg His Asp Phe Gly Phe Pro
610               615               620

Gln Glu Glu Phe Gly Asn Gln Phe Gln Lys Ala Glu Thr Ile Pro Val
625               630               635               640

Leu His Glu Met Ile Gln Gln Ile Phe Asn Leu Phe Ser Thr Lys Asp
            645               650               655

Ser Ser Ala Ala Trp Asp Glu Thr Leu Leu Asp Lys Phe Tyr Thr Glu
        660               665               670

Leu Tyr Gln Gln Leu Asn Asp Leu Glu Ala Cys Val Ile Gln Gly Val
675               680               685

Gly Val Thr Glu Thr Pro Leu Met Lys Glu Asp Ser Ile Leu Ala Val
690               695               700

Arg Lys Tyr Phe Gln Arg Ile Thr Leu Tyr Leu Lys Glu Lys Lys Tyr
705               710               715               720

Ser Pro Cys Ala Trp Glu Val Val Arg Ala Glu Ile Met Arg Ser Phe
            725               730               735

Ser Leu Ser Thr Asn Leu Gln Glu Ser Leu Arg Ser Lys Glu
        740               745               750
```

<210> SEQ ID NO 5
<211> LENGTH: 2322
<212> TYPE: DNA
<213> ORGANISM: Artificial Sequence
<220> FEATURE:
<223> OTHER INFORMATION: Synthesis

<400> SEQUENCE: 5

```
atgaagtggg taacctttat tccccttctt tttctcttta gctcggctta ttccaggggt      60
gtgtttcgtc gagatgcaca caagagtgag gttgctcatc ggtttaaaga tttgggagaa     120
gaaaatttca agccttggt gttgattgcc tttgctcagt atcttcagca gtgtccattt      180
gaagatcatg taaaattagt gaatgaagta actgaatttg caaaaacatg tgttgctgat    240
gagtcagctg aaaattgtga caaatcactt catacccttt ttggagacaa attatgcaca    300
gttgcaactc ttcgtgaaac ctatggtgaa atggctgact gctgtgcaaa acaagaacct    360
gagagaaatg aatgcttctt gcaacacaaa gatgacaacc caaacctccc ccgattggtg    420
```

-continued

```
agaccagagg ttgatgtgat gtgcactgct tttcatgaca atgaagagac attttttgaaa      480 aaatacttat atgaaattgc cagaagacat ccttactttt atgccccgga actccttttc      540
tttgctaaaa ggtataaagc tgcttttaca gaatgttgcc aagctgctga taaagctgcc      600
tgcctgttgc caaagctcga tgaacttcgg gatgaaggga aggcttcgtc tgccaaacag      660
agactcaagt gtgccagtct ccaaaaattt ggagaaagag ctttcaaagc atgggcagta      720
gctcgcctga gccagagatt tcccaaagct gagtttgcag aagtttccaa gttagtgaca      780
gatcttacca agtccacac ggaatgctgc catggagatc tgcttgaatg tgctgatgac       840
agggcggacc ttgccaagta tatctgtgaa atcaagatt cgatctccag taaactgaag        900
gaatgctgtg aaaaacctct gttggaaaaa tcccactgca ttgccgaagt ggaaaatgat      960
gagatgcctg ctgacttgcc ttcattagct gctgattttg ttgaaagtaa ggatgtttgc      1020
aaaaactatg ctgaggcaaa ggatgtcttc ctgggcatgt ttttgtatga atatgcaaga      1080
aggcatcctg attactctgt cgtgctgctg ctgagacttg ccaagacata tgaaaccact      1140
ctagagaagt gctgtgccgc tgcagatcct catgaatgct atgccaaagt gttcgatgaa      1200
tttaaacctc ttgtggaaga gcctcagaat ttaatcaaac aaaattgtga gcttttttgag     1260 cagcttggag agtacaaatt ccagaatgcg ctattagttc gttacaccaa gaaagtaccc      1320
caagtgtcaa ctccaactct tgtagaggtc tcaagaaacc taggaaaagt gggcagcaaa      1380
tgttgtaaac atcctgaagc aaaaagaatg ccctgtgcag aagactatct atccgtggtc      1440
ctgaaccagt tatgtgtgtt gcatgagaaa acgccagtaa gtgacagagt caccaaatgc      1500
tgcacagaat ccttggtgaa caggcgacca tgcttttcag ctctggaagt cgatgaaaca      1560
tacgttccca aagagtttaa tgctgaaaca ttcaccttcc atgcagatat atgcacactt      1620
tctgagaagg agagacaaat caagaaacaa actgcacttg ttgagcttgt gaaacacaag      1680
cccaaggcaa caaagagca actgaaagct gttatggatg atttcgcagc ttttgtagag       1740
aagtgctgca aggctgacga taaggagacc tgctttgccg aggagggtaa aaaacttgtt      1800
gctgcaagtc aagctgcctt aggcttatac aacttgcttg gattcctaca agaagcagc       1860 aattttcagt gtcagaagct cctgtggcaa ttgaatggga ggcttgaata ctgcctcaag      1920
gacaggatga acttttgacat ccctgaggag attaagcagc tgcagcagtt ccagaaggag     1980
gacgccgcat tgaccatcta tgagatgctc cagaacatct ttgctatttt cagacaagat      2040
tcatctagca ctggctggaa tgagactatt gttgagaacc tcctggctaa tgtctatcat      2100
cagataaacc atctgaagac agtcctggaa gaaaaactgg agaagaaga tttcaccagg       2160 ggaaaactca tgagcagtct gcacctgaaa agatattatg gaggattct gcattacctg       2220 aaggccaagg agtacagtca ctgtgcctgg accatagtca gagtggaaat cctaaggaac      2280
ttttacttca ttaacagact tacaggttac ctccgaaact ga                         2322
```

<210> SEQ ID NO 6
<211> LENGTH: 749
<212> TYPE: PRT
<213> ORGANISM: Artificial Sequence
<220> FEATURE:
<223> OTHER INFORMATION: Synthesis

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln

```
                    20              25              30
Gln Cys Pro Phe Glu Asp His Val Lys Leu Val Asn Glu Val Thr Glu
 35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
    100                 105                 110
Pro Arg Leu Val Arg Pro Glu Val Asp Val Met Cys Thr Ala Phe His
115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
    180                 185                 190
Ser Ala Lys Gln Arg Leu Lys Cys Ala Ser Leu Gln Lys Phe Gly Glu
195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
    260                 265                 270
Ser Lys Leu Lys Glu Cys Cys Glu Lys Pro Leu Leu Glu Lys Ser His
275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
    340                 345                 350
Tyr Glu Thr Thr Leu Glu Lys Cys Cys Ala Ala Ala Asp Pro His Glu
355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Glu Val Ser Thr Pro Thr Leu Val Glu Val Ser Arg Asn Leu Gly Lys
    420                 425                 430
Val Gly Ser Lys Cys Cys Lys His Pro Glu Ala Lys Arg Met Pro Cys
435                 440                 445
```

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
500                 505                 510

Ile Cys Thr Leu Ser Glu Lys Glu Arg Gln Ile Lys Lys Gln Thr Ala
515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Tyr Asn Leu Leu Gly Phe Leu
580                 585                 590

Gln Arg Ser Ser Asn Phe Gln Cys Gln Lys Leu Leu Trp Gln Leu Asn
595                 600                 605

Gly Arg Leu Glu Tyr Cys Leu Lys Asp Arg Met Asn Phe Asp Ile Pro
610                 615                 620

Glu Glu Ile Lys Gln Leu Gln Gln Phe Gln Lys Glu Asp Ala Ala Leu
625                 630                 635                 640

Thr Ile Tyr Glu Met Leu Gln Asn Ile Phe Ala Ile Phe Arg Gln Asp
            645                 650                 655

Ser Ser Ser Thr Gly Trp Asn Glu Thr Ile Val Glu Asn Leu Leu Ala
660                 665                 670

Asn Val Tyr His Gln Ile Asn His Leu Lys Thr Val Leu Glu Glu Lys
675                 680                 685

Leu Glu Lys Glu Asp Phe Thr Arg Gly Lys Leu Met Ser Ser Leu His
690                 695                 700

Leu Lys Arg Tyr Tyr Gly Arg Ile Leu His Tyr Leu Lys Ala Lys Glu
705                 710                 715                 720

Tyr Ser His Cys Ala Trp Thr Ile Val Arg Val Glu Ile Leu Arg Asn
            725                 730                 735

Phe Tyr Phe Ile Asn Arg Leu Thr Gly Tyr Leu Arg Asn
740                 745

<210> SEQ ID NO 7
<211> LENGTH: 2346
<212> TYPE: DNA
<213> ORGANISM: Artificial Sequence
<220> FEATURE:
<223> OTHER INFORMATION: Synthesis

<400> SEQUENCE: 7
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca agccttggt gttgattgcc tttgctcagt atcttcagca gtgtccattt     180
gaagatcatg taaaattagt gaatgaagta actgaatttg caaaaacatg tgttgctgat     240
gagtcagctg aaaattgtga caaatcactt catacccttt ttggagacaa attatgcaca     300
gttgcaactc ttcgtgaaac ctatggtgaa atggctgact gctgtgcaaa acaagaacct     360

```
gagagaaatg aatgcttctt gcaacacaaa gatgacaacc caaacctccc ccgattggtg      420
agaccagagg ttgatgtgat gtgcactgct tttcatgaca atgaagagac attttttgaaa     480 aaatacttat atgaaattgc cagaagacat ccttactttt atgccccgga actccttttc     540
tttgctaaaa ggtataaagc tgcttttaca gaatgttgcc aagctgctga taaagctgcc     600
tgcctgttgc caaagctcga tgaacttcgg gatgaaggga aggcttcgtc tgccaaacag     660
agactcaagt gtgccagtct ccaaaaattt ggagaaagag ctttcaaagc atgggcagta     720
gctcgcctga ccagagatt tcccaaagct gagtttgcag aagtttccaa gttagtgaca      780
gatcttacca aagtccacac ggaatgctgc catggagatc tgcttgaatg tgctgatgac     840
agggcggacc ttgccaagta tatctgtgaa aatcaagatt cgatctccag taaactgaag     900
gaatgctgtg aaaaacctct gttggaaaaa tcccactgca ttgccgaagt ggaaaatgat     960
gagatgcctg ctgacttgcc ttcattagct gctgattttg ttgaaagtaa ggatgtttgc    1020
aaaaactatg ctgaggcaaa ggatgtcttc ctgggcatgt ttttgtatga atatgcaaga    1080
aggcatcctg attactctgt cgtgctgctg ctgagacttg ccaagacata tgaaaccact    1140
ctagagaagt gctgtgccgc tgcagatcct catgaatgct atgccaaagt gttcgatgaa    1200
tttaaacctc ttgtggaaga gcctcagaat ttaatcaaac aaaattgtga gcttttgag     1260 cagcttggag agtacaaatt ccagaatgcg ctattagttc gttacaccaa gaaagtaccc    1320
caagtgtcaa ctccaactct tgtagaggtc tcaagaaacc taggaaaagt gggcagcaaa    1380
tgttgtaaac atcctgaagc aaaaagaatg ccctgtgcag aagactatct atccgtggtc    1440
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttatgt gatctgcctc agaaccatgg cctacttagc    1860
aggaacacct tggtgcttct gcaccaaatg aggagaatct ccccttctt gtgtctcaag     1920 gacagaagag acttcaggtt cccccaggag atggtaaaag ggagccagtt gcagaaggcc    1980
catgtcatgt ctgtcctcca tgagatgctg cagcagatct tcagcctctt ccacacagag    2040
cgctcctctg ctgcctggaa catgacccctc ctagaccaac tccacactgg acttcatcag   2100
caactgcaac acctggagac ctgcttgctg caggtagtgg gagaaggaga atctgctggg    2160
gcaattagca gccctgcact gaccttgagg aggtacttcc agggaatccg tgtctacctg    2220
aaagagaaga aatacagcga ctgtgcctgg gaagttgtca gaatggaaat catgaaatcc    2280
ttgttcttat caacaaacat gcaagaaaga ctgagaagta aagatagaga cctgggctca    2340
tcttga                                                               2346

<210> SEQ ID NO 8
<211> LENGTH: 757
<212> TYPE: PRT
<213> ORGANISM: Artificial Sequence
<220> FEATURE:
<223> OTHER INFORMATION: synthesis

<400> SEQUENCE: 8
```

-continued

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
            85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
            165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
260                 265                 270

Ser Lys Leu Lys Glu Cys Cys Glu Lys Pro Leu Leu Glu Lys Ser His
275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Glu Val Ser Thr Pro Thr Leu Val Glu Val Ser Arg Asn Leu Gly Lys
```

-continued

```
            420             425             430
Val Gly Ser Lys Cys Cys Lys His Pro Glu Ala Lys Arg Met Pro Cys
435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Cys Asp Leu Pro Gln Asn His
        580                 585                 590

Gly Leu Leu Ser Arg Asn Thr Leu Val Leu Leu His Gln Met Arg Arg
595                 600                 605

Ile Ser Pro Phe Leu Cys Leu Lys Asp Arg Arg Asp Phe Arg Phe Pro
610                 615                 620

Gln Glu Met Val Lys Gly Ser Gln Leu Gln Lys Ala His Val Met Ser
625                 630                 635                 640

Val Leu His Glu Met Leu Gln Gln Ile Phe Ser Leu Phe His Thr Glu
                645                 650                 655

Arg Ser Ser Ala Ala Trp Asn Met Thr Leu Leu Asp Gln Leu His Thr
        660                 665                 670

Gly Leu His Gln Gln Leu Gln His Leu Glu Thr Cys Leu Leu Gln Val
675                 680                 685

Val Gly Glu Gly Glu Ser Ala Gly Ala Ile Ser Ser Pro Ala Leu Thr
690                 695                 700

Leu Arg Arg Tyr Phe Gln Gly Ile Arg Val Tyr Leu Lys Glu Lys Lys
705                 710                 715                 720

Tyr Ser Asp Cys Ala Trp Glu Val Val Arg Met Glu Ile Met Lys Ser
                725                 730                 735

Leu Phe Leu Ser Thr Asn Met Gln Glu Arg Leu Arg Ser Lys Asp Arg
        740                 745                 750

Asp Leu Gly Ser Ser
755

<210> SEQ ID NO 9
<211> LENGTH: 2259
<212> TYPE: DNA
<213> ORGANISM: Artificial Sequence
<220> FEATURE:
<223> OTHER INFORMATION: synthesis

<400> SEQUENCE: 9
atgaagtggg taacctttat ttcccttctt tttctctttt gctcggctta ttccaggggt      60
gtgtttcgtc gagatgcaca caagagtgag gttgctcatc ggtttaaaga tttgggagaa     120
```

-continued

```
gaaaatttca aagccttggt gttgattgcc tttgctcagt atcttcagca gtgtccattt      180
gaagatcatg taaaattagt gaatgaagta actgaatttg caaaaacatg tgttgctgat      240
gagtcagctg aaaattgtga caaatcactt catacccttt ttggagacaa attatgcaca      300
gttgcaactc ttcgtgaaac ctatggtgaa atggctgact gctgtgcaaa acaagaacct      360
gagagaaatg aatgcttctt gcaacacaaa gatgacaacc caaacctccc ccgattggtg      420
agaccagagg ttgatgtgat gtgcactgct tttcatgaca atgaagagac attttttgaaa     480 aaatacttat atgaaattgc cagaagacat ccttactttt atgccccgga actccttttc      540
tttgctaaaa ggtataaagc tgcttttaca gaatgttgcc aagctgctga taaagctgcc      600
tgcctgttgc caaagctcga tgaacttcgg gatgaaggga aggcttcgtc tgccaaacag      660
agactcaagt gtgccagtct ccaaaaattt ggagaaagag ctttcaaagc atgggcagta      720
gctcgcctga gccagagatt tcccaaagct gagtttgcag aagtttccaa gttagtgaca      780
gatcttacca aagtccacac ggaatgctgc catggagatc tgcttgaatg tgctgatgac      840
agggcggacc ttgccaagta tatctgtgaa aatcaagatt cgatctccag taaactgaag      900
gaatgctgtg aaaaacctct gttggaaaaa tcccactgca ttgccgaagt ggaaaatgat      960
gagatgcctg ctgacttgcc ttcattagct gctgattttg ttgaaagtaa ggatgtttgc     1020
aaaaactatg ctgaggcaaa ggatgtcttc ctgggcatgt ttttgtatga atatgcaaga     1080
aggcatcctg attactctgt cgtgctgctg ctgagacttg ccaagacata tgaaaccact     1140
ctagagaagt gctgtgccgc tgcagatcct catgaatgct atgccaaagt gttcgatgaa     1200
tttaaacctc ttgtggaaga gcctcagaat ttaatcaaac aaaattgtga gcttttttgag    1260 cagcttggag agtacaaatt ccagaatgcg ctattagttc gttacaccaa gaaagtaccc     1320
caagtgtcaa ctccaactct tgtagaggtc tcaagaaacc taggaaaagt gggcagcaaa     1380
tgttgtaaac atcctgaagc aaaaagaatg ccctgtgcag aagactatct atccgtggtc     1440
ctgaaccagt tatgtgtgtt gcatgagaaa acgccagtaa gtgacagagt caccaaatgc     1500
tgcacagaat ccttggtgaa caggcgacca tgcttttcag ctctggaagt cgatgaaaca     1560
tacgttccca aagagtttaa tgctgaaaca ttcaccttcc atgcagatat atgcacactt     1620
tctgagaagg agagacaaat caagaaacaa actgcacttg ttgagcttgt gaaacacaag     1680
cccaaggcaa caaagagca actgaaagct gttatggatg atttcgcagc ttttgtagag      1740
aagtgctgca aggctgacga taaggagacc tgctttgccg aggagggtaa aaaacttgtt     1800
gctgcaagtc aagctgcctt aggcttacag gacccatatg tacaagaagc agaaaacctt     1860
aagaaatatt ttaatgcagg tcattcagat gtagcggata atggaactct tttcttaggc     1920
attttgaaga attggaaaga ggagagtgac agaaaaataa tgcagagcca aattgtctcc     1980
ttttacttca aactttttaa aaactttaaa gatgaccaga gcatccaaaa gagtgtggag     2040
accatcaagg aagacatgaa tgtcaagttt ttcaatagca caaaaagaa acgagatgac      2100 ttcgaaaagc tgactaatta ttcggtaact gacttgaatg tccaacgcaa agcaatacat     2160
gaactcatcc aagtgatggc tgaactgtcg ccagcagcta aaacagggaa gcgaaaaagg     2220
agtcagatgc tgtttcgagg tcgaagagca tcccagtaa                            2259
```

<210> SEQ ID NO 10
<211> LENGTH: 728
<212> TYPE: PRT
<213> ORGANISM: Artificial Sequence
<220> FEATURE:
<223> OTHER INFORMATION: synthesis

```
<400> SEQUENCE: 10

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
```

-continued

```
            405                 410                 415
Glu Val Ser Thr Pro Thr Leu Val Glu Val Ser Arg Asn Leu Gly Lys
        420                 425                 430
Val Gly Ser Lys Cys Cys Lys His Pro Glu Ala Lys Arg Met Pro Cys
435                 440                 445
Ala Glu Asp Tyr Leu Ser Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
        500                 505                 510
Ile Cys Thr Leu Ser Glu Lys Glu Arg Gln Ile Lys Lys Gln Thr Ala
515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gln Asp Pro Tyr Val Gln Glu
        580                 585                 590
Ala Glu Asn Leu Lys Lys Tyr Phe Asn Ala Gly His Ser Asp Val Ala
595                 600                 605
Asp Asn Gly Thr Leu Phe Leu Gly Ile Leu Lys Asn Trp Lys Glu Glu
610                 615                 620
Ser Asp Arg Lys Ile Met Gln Ser Gln Ile Val Ser Phe Tyr Phe Lys
625                 630                 635                 640
Leu Phe Lys Asn Phe Lys Asp Asp Gln Ser Ile Gln Lys Ser Val Glu
                645                 650                 655
Thr Ile Lys Glu Asp Met Asn Val Lys Phe Phe Asn Ser Asn Lys Lys
        660                 665                 670
Lys Arg Asp Asp Phe Glu Lys Leu Thr Asn Tyr Ser Val Thr Asp Leu
675                 680                 685
Asn Val Gln Arg Lys Ala Ile His Glu Leu Ile Gln Val Met Ala Glu
690                 695                 700
Leu Ser Pro Ala Ala Lys Thr Gly Lys Arg Lys Arg Ser Gln Met Leu
705                 710                 715                 720
Phe Arg Gly Arg Arg Ala Ser Gln
        725
```

<210> SEQ ID NO 11
<211> LENGTH: 1830
<212> TYPE: DNA
<213> ORGANISM: Homo sapiens

<400> SEQUENCE: 11

```
atgaagtggg taacctttat ttcccttctt tttctcttta gctcggctta ttccaggggt    60
gtgtttcgtc gagatgcaca caagagtgag gttgctcatc ggtttaaaga tttgggagaa   120
gaaaatttca agccttggt gttgattgcc tttgctcagt atcttcagca gtgtccattt   180
gaagatcatg taaaattagt gaatgaagta actgaatttg caaaaacatg tgttgctgat   240
gagtcagctg aaaattgtga caaatcactt catacccttt ttggagacaa attatgcaca   300
```

-continued

```
gttgcaactc ttcgtgaaac ctatggtgaa atggctgact gctgtgcaaa acaagaacct      360
gagagaaatg aatgcttctt gcaacacaaa gatgacaacc caaacctccc ccgattggtg      420
agaccagagg ttgatgtgat gtgcactgct tttcatgaca atgaagagac attttttgaaa    480
aaatacttat atgaaattgc cagaagacat ccttactttt atgccccgga actccttttc      540
tttgctaaaa ggtataaagc tgcttttaca gaatgttgcc aagctgctga taaagctgcc      600
tgcctgttgc caaagctcga tgaacttcgg gatgaaggga aggcttcgtc tgccaaacag      660
agactcaagt gtgccagtct ccaaaaattt ggagaaagag ctttcaaagc atgggcagta      720
gctcgcctga ccagagatt tcccaaagct gagtttgcag aagtttccaa gttagtgaca       780
gatcttacca agtccacac ggaatgctgc catggagatc tgcttgaatg tgctgatgac        840
agggcggacc ttgccaagta tatctgtgaa aatcaagatt cgatctccag taaactgaag      900
gaatgctgtg aaaaacctct gttggaaaaa tcccactgca ttgccgaagt ggaaaatgat      960
gagatgcctg ctgacttgcc ttcattagct gctgattttg ttgaaagtaa ggatgtttgc     1020
aaaaactatg ctgaggcaaa ggatgtcttc ctgggcatgt ttttgtatga atatgcaaga     1080
aggcatcctg attactctgt cgtgctgctg ctgagacttg ccaagacata tgaaaccact     1140
ctagagaagt gctgtgccgc tgcagatcct catgaatgct atgccaaagt gttcgatgaa     1200
tttaaacctc ttgtggaaga gcctcagaat ttaatcaaac aaaattgtga gcttttttgag     1260
cagcttggag agtacaaatt ccagaatgcg ctattagttc gttacaccaa gaaagtaccc     1320
caagtgtcaa ctccaactct tgtagaggtc tcaagaaacc taggaaaagt gggcagcaaa     1380
tgttgtaaac atcctgaagc aaaaagaatg ccctgtgcag aagactatct atccgtggtc     1440
ctgaaccagt tatgtgtgtt gcatgagaaa acgccagtaa gtgacagagt caccaaatgc     1500
tgcacagaat ccttggtgaa caggcgacca tgcttttcag ctctggaagt cgatgaaaca     1560
tacgttccca agagtttaa tgctgaaaca ttcaccttcc atgcagatat atgcacactt      1620
tctgagaagg agagacaaat caagaaacaa actgcacttg ttgagcttgt gaaacacaag     1680
cccaaggcaa caaagagca actgaaagct gttatggatg atttcgcagc ttttgtagag      1740
aagtgctgca aggctgacga taaggagacc tgctttgccg aggagggtaa aaaacttgtt     1800
gctgcaagtc aagctgcctt aggcttataa                                     1830
```

<210> SEQ ID NO 12
<211> LENGTH: 585
<212> TYPE: PRT
<213> ORGANISM: Homo sapiens

<400> SEQUENCE: 12

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

-continued

```
Glu Arg Asn Glu Cys Phe Leu Gln His Lys Asp Asp Asn Pro Asn Leu
    100                 105                 110
Pro Arg Leu Val Arg Pro Glu Val Asp Val Met Cys Thr Ala Phe His
115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
    180                 185                 190
Ser Ala Lys Gln Arg Leu Lys Cys Ala Ser Leu Gln Lys Phe Gly Glu
195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
    260                 265                 270
Ser Lys Leu Lys Glu Cys Cys Glu Lys Pro Leu Leu Glu Lys Ser His
275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
    340                 345                 350
Tyr Glu Thr Thr Leu Glu Lys Cys Cys Ala Ala Ala Asp Pro His Glu
355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Glu Val Ser Thr Pro Thr Leu Val Glu Val Ser Arg Asn Leu Gly Lys
    420                 425                 430
Val Gly Ser Lys Cys Cys Lys His Pro Glu Ala Lys Arg Met Pro Cys
435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
    500                 505                 510
Ile Cys Thr Leu Ser Glu Lys Glu Arg Gln Ile Lys Lys Gln Thr Ala
```

```
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
            565                 570                 575
Ala Ala Ser Gln Ala Ala Leu Gly Leu
        580                 585

<210> SEQ ID NO 13
<211> LENGTH: 567
<212> TYPE: DNA
<213> ORGANISM: Homo sapiens

<400> SEQUENCE: 13
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggagaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagaccctcc tagacaaatt ctacactgaa ctctaccagc agctgaatga cctggaagcc     360
tgtgtgatac aggggtgggg ggtgacagag actcccctga tgaaggagga ctccattctg     420
gctgtgagga atacttcca agaatcact ctctatctga agagaagaa atacagccct        480 tgtgcctggg aggttgtcag agcagaaatc atgagatctt tttctttgtc aacaaacttg     540
caagaaagtt taagaagtaa ggaatga                                         567

<210> SEQ ID NO 14
<211> LENGTH: 188
<212> TYPE: PRT
<213> ORGANISM: Homo sapiens

<400> SEQUENCE: 14

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
35                  40                  45

Leu Phe Ser Cys Leu Lys Asp Arg His Asp Phe Gly Phe Pro Gln Glu
50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
            85                  90                  95

Ala Ala Trp Asp Glu Thr Leu Leu Asp Lys Phe Tyr Thr Glu Leu Tyr
        100                 105                 110

Gln Gln Leu Asn Asp Leu Glu Ala Cys Val Ile Gln Gly Val Gly Val
    115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160
```

Cys Ala Trp Glu Val Val Arg Ala Glu Ile Met Arg Ser Phe Ser Leu
            165                 170                 175

Ser Thr Asn Leu Gln Glu Ser Leu Arg Ser Lys Glu
        180                 185

<210> SEQ ID NO 15
<211> LENGTH: 567
<212> TYPE: DNA
<213> ORGANISM: Homo sapiens

<400> SEQUENCE: 15
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggaaaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagaccctcc tagacaaatt ctacactgaa ctctaccagc agctgaatga cctggaagcc     360
tgtgtgatac agggggtggg ggtgacagag actcccctga tgaaggagga ctccattctg     420
gctgtgagga aatacttcca agaatcact ctctatctga agagaagaa atacagccct       480 tgtgcctggg aggttgtcag agcagaaatc atgagatctt ttctttgtc aacaaacttg     540 caagaaagtt taagaagtaa ggaatga                                         567

<210> SEQ ID NO 16
<211> LENGTH: 188
<212> TYPE: PRT
<213> ORGANISM: Homo sapiens

<400> SEQUENCE: 16

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Lys Ile Ser
35                  40                  45

Leu Phe Ser Cys Leu Lys Asp Arg His Asp Phe Gly Phe Pro Gln Glu
50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
            85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
            165                 170                 175

Ser Thr Asn Leu Gln Glu Ser Leu Arg Ser Lys Glu
        180                 185

<210> SEQ ID NO 17
<211> LENGTH: 564
<212> TYPE: DNA
<213> ORGANISM: Homo sapiens

<400> SEQUENCE: 17

```
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tactgcctca aggacaggat gaactttgac     180
atccctgagg agattaagca gctgcagcag ttccagaagg aggacgccgc attgaccatc     240
tatgagatgc tccagaacat ctttgctatt ttcagacaag attcatctag cactggctgg     300
aatgagacta ttgttgagaa cctcctggct aatgtctatc atcagataaa ccatctgaag     360
acagtcctgg aagaaaaact ggagaaagaa gatttcacca ggggaaaact catgagcagt     420
ctgcacctga aagatatta tgggaggatt ctgcattacc tgaaggccaa ggagtacagt     480
cactgtgcct ggaccatagt cagagtggaa atcctaagga acttttactt cattaacaga     540
cttacaggtt acctccgaaa ctga                                            564
```

<210> SEQ ID NO 18
<211> LENGTH: 187
<212> TYPE: PRT
<213> ORGANISM: Homo sapiens

<400> SEQUENCE: 18

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
35                  40                  45

Leu Glu Tyr Cys Leu Lys Asp Arg Met Asn Phe Asp Ile Pro Glu Glu
50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
            85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
115                 120                 125

Lys Glu Asp Phe Thr Arg Gly Lys Leu Met Ser Ser Leu His Leu Lys
130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
            165                 170                 175

Phe Ile Asn Arg Leu Thr Gly Tyr Leu Arg Asn
            180                 185

<210> SEQ ID NO 19
<211> LENGTH: 588
<212> TYPE: DNA
<213> ORGANISM: Homo sapiens

<400> SEQUENCE: 19

```
atggccctcc tgttccctct actggcagcc ctagtgatga ccagctatag ccctgttgga      60
tctctgggct gtgatctgcc tcagaaccat ggcctactta gcaggaacac cttggtgctt     120
ctgcaccaaa tgaggagaat ctcccctttc ttgtgtctca aggacagaag agacttcagg     180
ttcccccagg agatggtaaa agggagccag ttgcagaagg cccatgtcat gtctgtcctc     240
catgagatgc tgcagcagat cttcagcctc ttccacacag agcgctcctc tgctgcctgg     300
aacatgaccc tcctagacca actccacact ggacttcatc agcaactgca cacctggag      360 acctgcttgc tgcaggtagt gggagaagga gaatctgctg ggcaattag cagccctgca      420 ctgaccttga ggaggtactt ccagggaatc cgtgtctacc tgaaagagaa gaaatacagc     480
gactgtgcct gggaagttgt cagaatggaa atcatgaaat ccttgttctt atcaacaaac     540
atgcaagaaa gactgagaag taaagataga gacctgggct catcttga                 588
```

<210> SEQ ID NO 20
<211> LENGTH: 194
<212> TYPE: PRT
<213> ORGANISM: Homo sapiens

<400> SEQUENCE: 20

```
Ala Leu Leu Phe Pro Leu Leu Ala Ala Leu Val Met Thr Ser Tyr Ser
1               5                   10                  15

Pro Val Gly Ser Leu Gly Cys Asp Leu Pro Gln Asn His Gly Leu Leu
            20                  25                  30

Ser Arg Asn Thr Leu Val Leu Leu His Gln Met Arg Arg Ile Ser Pro
35                  40                  45

Phe Leu Cys Leu Lys Asp Arg Arg Asp Phe Arg Phe Pro Gln Glu Met
50                  55                  60

Val Lys Gly Ser Gln Leu Gln Lys Ala His Val Met Ser Val Leu His
65                  70                  75                  80

Glu Met Leu Gln Gln Ile Phe Ser Leu Phe His Thr Glu Arg Ser Ser
                85                  90                  95

Ala Ala Trp Asn Met Thr Leu Leu Asp Gln Leu His Thr Gly Leu His
            100                 105                 110

Gln Gln Leu Gln His Leu Glu Thr Cys Leu Leu Gln Val Val Gly Glu
115                 120                 125

Gly Glu Ser Ala Gly Ala Ile Ser Ser Pro Ala Leu Thr Leu Arg Arg
130                 135                 140

Tyr Phe Gln Gly Ile Arg Val Tyr Leu Lys Glu Lys Lys Tyr Ser Asp
145                 150                 155                 160

Cys Ala Trp Glu Val Val Arg Met Glu Ile Met Lys Ser Leu Phe Leu
                165                 170                 175

Ser Thr Asn Met Gln Glu Arg Leu Arg Ser Lys Asp Arg Asp Leu Gly
            180                 185                 190

Ser Ser
```

<210> SEQ ID NO 21
<211> LENGTH: 501
<212> TYPE: DNA
<213> ORGANISM: Homo sapiens

<400> SEQUENCE: 21

```
atgaaatata caagttatat cttggctttt cagctctgca tcgttttggg ttctcttggc     60
tgttactgcc aggacccata tgtacaagaa gcagaaaacc ttaagaaata ttttaatgca   120
```

```
ggtcattcag atgtagcgga taatggaact cttttcttag cattttgaa gaattggaaa      180 gaggagagtg acagaaaaat aatgcagagc caaattgtct cctttcactt caaacttttt    240
```

```
ggtcattcag atgtagcgga taatggaact cttttcttag cattttgaa gaattggaaa      180 gaggagagtg acagaaaaat aatgcagagc caaattgtct ccttttactt caaacttttt    240
aaaaacttta aagatgacca gagcatccaa aagagtgtgg agaccatcaa ggaagacatg    300
aatgtcaagt ttttcaatag caacaaaaag aaacgagatg acttcgaaaa gctgactaat    360
tattcggtaa ctgacttgaa tgtccaacgc aaagcaatac atgaactcat ccaagtgatg    420
gctgaactgt cgccagcagc taaaacaggg aagcgaaaaa ggagtcagat gctgtttcga    480
ggtcgaagag catcccagta a                                              501
```

<210> SEQ ID NO 22
<211> LENGTH: 166
<212> TYPE: PRT
<213> ORGANISM: Homo sapiens

<400> SEQUENCE: 22

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Gln Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 23
<211> LENGTH: 30
<212> TYPE: DNA
<213> ORGANISM: Artificial Sequence
<220> FEATURE:
<223> OTHER INFORMATION: synthesis

<400> SEQUENCE: 23
gaattcatga agtgggtaac ctttatttcc                                      30

<210> SEQ ID NO 24
<211> LENGTH: 25
<212> TYPE: DNA
<213> ORGANISM: Artificial Sequence
<220> FEATURE:
<223> OTHER INFORMATION: synthesis

<400> SEQUENCE: 24
catatgtgtg atctccctga gaccc                                           25

```
<210> SEQ ID NO 25
<211> LENGTH: 25
<212> TYPE: DNA
<213> ORGANISM: Artificial Sequence
<220> FEATURE:
<223> OTHER INFORMATION: synthesis

<400> SEQUENCE: 25
catatgtgtg atctccctga gaccc                                           25

<210> SEQ ID NO 26
<211> LENGTH: 27
<212> TYPE: DNA
<213> ORGANISM: Artificial Sequence
<220> FEATURE:
<223> OTHER INFORMATION: synthesis

<400> SEQUENCE: 26
ggatccttac ttcctcctta atctttc                                         27

<210> SEQ ID NO 27
<211> LENGTH: 25
<212> TYPE: DNA
<213> ORGANISM: Artificial Sequence
<220> FEATURE:
<223> OTHER INFORMATION: synthesis

<400> SEQUENCE: 27
catatggcct tgacctttgc tttac                                           25

<210> SEQ ID NO 28
<211> LENGTH: 26
<212> TYPE: DNA
<213> ORGANISM: Artificial Sequence
<220> FEATURE:
<223> OTHER INFORMATION: synthesis

<400> SEQUENCE: 28
ggatcctcat tccttacttc ttaaac                                          26

<210> SEQ ID NO 29
<211> LENGTH: 35
<212> TYPE: DNA
<213> ORGANISM: Artificial Sequence
<220> FEATURE:
<223> OTHER INFORMATION: synthesis

<400> SEQUENCE: 29
tggcacagat gaggaaaatc tctcttttct cctgc                                35

<210> SEQ ID NO 30
<211> LENGTH: 36
<212> TYPE: DNA
<213> ORGANISM: Artificial Sequence
<220> FEATURE:
<223> OTHER INFORMATION: synthesis

<400> SEQUENCE: 30
caggagaaaa gagagatttt cctcatctgt gccagc                               36

<210> SEQ ID NO 31
<211> LENGTH: 22
<212> TYPE: DNA
<213> ORGANISM: Artificial Sequence
<220> FEATURE:
<223> OTHER INFORMATION: synthesis
```

<400> SEQUENCE: 31
catatgacca acaagtgtct cc                                          22

<210> SEQ ID NO 32
<211> LENGTH: 24
<212> TYPE: DNA
<213> ORGANISM: Artificial Sequence
<220> FEATURE:
<223> OTHER INFORMATION: synthesis

<400> SEQUENCE: 32
gaattctcag tttcggaggt aacc                                        24

<210> SEQ ID NO 33
<211> LENGTH: 25
<212> TYPE: DNA
<213> ORGANISM: Artificial Sequence
<220> FEATURE:
<223> OTHER INFORMATION: synthesis

<400> SEQUENCE: 33
catatggccc tcctgttccc tctac                                       25

<210> SEQ ID NO 34
<211> LENGTH: 26
<212> TYPE: DNA
<213> ORGANISM: Artificial Sequence
<220> FEATURE:
<223> OTHER INFORMATION: synthesis

<400> SEQUENCE: 34
gaattctcaa gatgagccca ggtctc                                      26

<210> SEQ ID NO 35
<211> LENGTH: 24
<212> TYPE: DNA
<213> ORGANISM: Artificial Sequence
<220> FEATURE:
<223> OTHER INFORMATION: synthesis

<400> SEQUENCE: 35
catatgaaat atacaagtta tatc                                        24

<210> SEQ ID NO 36
<211> LENGTH: 24
<212> TYPE: DNA
<213> ORGANISM: Artificial Sequence
<220> FEATURE:
<223> OTHER INFORMATION: synthesis

<400> SEQUENCE: 36
gaattcttac tgggatgctc ttcg                                        24

<210> SEQ ID NO 37
<211> LENGTH: 33
<212> TYPE: DNA
<213> ORGANISM: Artificial Sequence
<220> FEATURE:
<223> OTHER INFORMATION: synthesis

<400> SEQUENCE: 37
ctgccttagg cttatgtgat ctccctgaga ccc                              33

<210> SEQ ID NO 38

```
<211> LENGTH: 28
<212> TYPE: DNA
<213> ORGANISM: Artificial Sequence
<220> FEATURE:
<223> OTHER INFORMATION: synthesis

<400> SEQUENCE: 38
tctcgagtta cttcctcctt aatctttc                                          28

<210> SEQ ID NO 39
<211> LENGTH: 33
<212> TYPE: DNA
<213> ORGANISM: Artificial Sequence
<220> FEATURE:
<223> OTHER INFORMATION: synthesis

<400> SEQUENCE: 39
ctgccttagg cttatgtgat ctgcctcaaa ccc                                    33

<210> SEQ ID NO 40
<211> LENGTH: 27
<212> TYPE: DNA
<213> ORGANISM: Artificial Sequence
<220> FEATURE:
<223> OTHER INFORMATION: synthesis

<400> SEQUENCE: 40
tctcgagtca ttccttactt cttaaac                                           27

<210> SEQ ID NO 41
<211> LENGTH: 33
<212> TYPE: DNA
<213> ORGANISM: Artificial Sequence
<220> FEATURE:
<223> OTHER INFORMATION: synthesis

<400> SEQUENCE: 41
ctgccttagg cttatacaac ttgcttggat tcc                                    33

<210> SEQ ID NO 42
<211> LENGTH: 26
<212> TYPE: DNA
<213> ORGANISM: Artificial Sequence
<220> FEATURE:
<223> OTHER INFORMATION: synthesis

<400> SEQUENCE: 42
cactcgagtc agtttcggag gtaacc                                            26

<210> SEQ ID NO 43
<211> LENGTH: 37
<212> TYPE: DNA
<213> ORGANISM: Artificial Sequence
<220> FEATURE:
<223> OTHER INFORMATION: synthesis

<400> SEQUENCE: 43
ctgccttagg cttatgtgat ctgcctcaga accatgg                                37

<210> SEQ ID NO 44
<211> LENGTH: 26
<212> TYPE: DNA
<213> ORGANISM: Artificial Sequence
<220> FEATURE:
<223> OTHER INFORMATION: synthesis

<400> SEQUENCE: 44
```

```
ctcgagtcaa gatgagccca ggtctc                                          26

<210> SEQ ID NO 45
<211> LENGTH: 37
<212> TYPE: DNA
<213> ORGANISM: Artificial Sequence
<220> FEATURE:
<223> OTHER INFORMATION: synthesis

<400> SEQUENCE: 45
actccttagg cttacaggac ccatatgtac aagaagc                              37

<210> SEQ ID NO 46
<211> LENGTH: 24
<212> TYPE: DNA
<213> ORGANISM: Artificial Sequence
<220> FEATURE:
<223> OTHER INFORMATION: synthesis

<400> SEQUENCE: 46
ctcgagttac tgggatgctc ttcg                                            24
```